United States Patent
Alemany Bonastre et al.

(10) Patent No.: US 11,578,104 B2
(45) Date of Patent: *Feb. 14, 2023

(54) ADENOVIRUS COMPRISING AN ALBUMIN-BINDING MOIETY

(71) Applicants: Fundacio Privada Institut D'Investigacio Biomedica De Bellvitge (IDIBELL), Barcelona (ES); INSTITUT CATALÀ D'ONCOLOGIA (ICO), Barcelona (ES)

(72) Inventors: Ramon Alemany Bonastre, Castelldefels-Barcelona (ES); Luis Alfonso Rojas Expósito, Sabadell (ES)

(73) Assignees: Fundació Institut D'lnvestigació Biomedica De Bellvitge (í DIBELL), Barcelona (ES); INSTITUT CATALA D'ONCOLOGIA (ICO), Barcelona (ES)

( * ) Notice: Subject to any disclaimer, the term of this patent is extended or adjusted under 35 U.S.C. 154(b) by 411 days.

This patent is subject to a terminal disclaimer.

(21) Appl. No.: 16/795,478

(22) Filed: Feb. 19, 2020

(65) Prior Publication Data

US 2020/0181208 A1   Jun. 11, 2020

Related U.S. Application Data

(63) Continuation of application No. 15/307,408, filed as application No. PCT/EP2015/059593 on Apr. 30, 2015, now Pat. No. 10,604,549.

(30) Foreign Application Priority Data

Apr. 30, 2014  (EP) .................................. 14382162.7

(51) Int. Cl.
   *C07K 14/315* (2006.01)
   *C12N 7/00* (2006.01)
   *A61K 35/761* (2015.01)
   *C07K 14/005* (2006.01)
   *C07K 14/075* (2006.01)
   *A61K 48/00* (2006.01)

(52) U.S. Cl.
   CPC .......... *C07K 14/315* (2013.01); *A61K 35/761* (2013.01); *C07K 14/005* (2013.01); *C07K 14/075* (2013.01); *C12N 7/00* (2013.01); *A61K 48/00* (2013.01); *C07K 2319/00* (2013.01); *C07K 2319/10* (2013.01); *C07K 2319/31* (2013.01); *C07K 2319/70* (2013.01); *C12N 2710/10321* (2013.01); *C12N 2710/10322* (2013.01); *C12N 2710/10332* (2013.01); *C12N 2710/10334* (2013.01); *C12N 2710/10343* (2013.01); *C12N 2710/10371* (2013.01)

(58) Field of Classification Search
   None
   See application file for complete search history.

(56) References Cited

U.S. PATENT DOCUMENTS

| | | | |
|---|---|---|---|
| 4,677,063 A | 6/1987 | Mark et al. | |
| 4,727,138 A | 2/1988 | Goeddel et al. | |
| 4,738,927 A | 4/1988 | Taniguchi et al. | |
| 4,762,791 A | 8/1988 | Goeddel et al. | |
| 4,965,195 A | 10/1990 | Namen et al. | |
| 5,328,988 A | 7/1994 | Namen et al. | |
| 5,391,485 A | 2/1995 | Deeley et al. | |
| 5,393,870 A | 2/1995 | Deeley et al. | |
| 5,457,038 A | 10/1995 | Trinchieri et al. | |
| 5,641,665 A | 6/1997 | Hobart et al. | |
| 5,773,582 A | 6/1998 | Shin et al. | |
| 5,801,029 A | 9/1998 | McCormick | |
| 5,998,205 A | 12/1999 | Hallenbeck et al. | |
| 10,604,549 B2 | 3/2020 | Bonastre et al. | |
| 2004/0091456 A1 | 5/2004 | Nakai et al. | |
| 2008/0112929 A1 | 5/2008 | Kovesdi et al. | |
| 2009/0068202 A1 | 3/2009 | Chen et al. | |
| 2012/0148535 A1 | 6/2012 | Carrio et al. | |

FOREIGN PATENT DOCUMENTS

| | | |
|---|---|---|
| CN | 1439055 A | 8/2003 |
| CN | 101781636 A | 7/2010 |
| CN | 101802013 A | 8/2010 |
| CN | 102548584 A | 7/2012 |
| EP | 2012822 B1 | 1/2010 |
| WO | 0145746 A2 | 6/2001 |
| WO | 0208263 A2 | 1/2002 |
| WO | 2007050128 A2 | 5/2007 |
| WO | 2011129468 A9 | 10/2011 |

OTHER PUBLICATIONS

Alemany, R., et al., "Blood clearance rates of adenovirus type 5 in mice", "Journal of General Virology", Jul. 24, 2000, pp. 2605-2609, vol. 81.

Alemany, R., "Design of Improved Oncolytic Adenoviruses", "Advances in Cancer Research", 2012, pp. 93-114, vol. 115.

Andersen, J.T., et al., "Extending Half-life by Indirect Targeting of the Neonatal Fc Receptor (FcRn) Using a Minimum Albumin Binding Domain", "The Journal of Biological Chemistry", Feb. 18, 2011, pp. 5234-5241, vol. 286, No. 7.

Bayo-Puxan, N., et al., "Replacement of Adenovirus Type 5 Fiber Shaft Heparan Sulfate Proteoglycan-Binding Domain with RGD for Improved Tumor Infectivity and Targeting", "Human Gene Therapy", Aug. 6, 2009, pp. 1214-1221, vol. 20.

(Continued)

*Primary Examiner* — James D Schultz
(74) *Attorney, Agent, or Firm* — Morgan, Lewis & Bockius LLP

(57) ABSTRACT

The invention relates to a recombinant adenovirus comprising an albumin-binding moiety on the outer surface of the adenoviral hexon protein, pharmaceutical compositions containing it and its medical use. Particularly, the invention relates to an oncolytic adenovirus comprising a sequence encoding an albumin-binding moiety inserted in the hypervariable region 1 (HVR1) of the hexon protein coding sequence and its use in the prevention and/or treatment of cancer.

16 Claims, 10 Drawing Sheets

Specification includes a Sequence Listing.

(56) References Cited

OTHER PUBLICATIONS

Biere, B., et al., "Human adenoviruses in respiratory infections: Sequencing of the hexon hypervariable region reveals high sequence variability", "Journal of Clinical Virology", Jan. 9, 2010, pp. 366-371, vol. 47.

Blaese, R.M., et al., "In situ Delivery of Suicide Genes for Cancer Treatment", "European Journal of Cancer", May 26, 1994, pp. 1190-1193, vol. 30A, No. 8.

Carlisle, R.C., et al., "Human erythrocytes bind and inactivate type 5 adenovirus by presenting Coxsackie virus-adenovirus receptor and complement receptor 1", "Gene Therapy", Feb. 26, 2009, pp. 1909-1918, vol. 113, No. 9.

Cascallo, M., et al., "Systemic Toxicity-Efficacy Profile of ICOVIR-5, a Potent and Selective Oncolytic Adenovirus Based on the pRB Pathway", "Molecular Therapy", Sep. 2007, pp. 1607-1615, vol. 15, No. 9.

Coughlan, L., et al., "Tropism-Modification Strategies for Targeted Gene Delivery Using Adenoviral Vectors", "Viruses", Oct. 13, 2010, pp. 2290-2355, doi:10.3390/v2102290, vol. 2.

Crawford-Miksza, L., et al., "Analysis of 15 Adenovirus Hexon Proteins Reveals the Location and Structure of Seven Hypervariable Regions Containing Serotype-Specific Residues", "Journal of Virology", Mar. 1996, pp. 1836-1844, vol. 70, No. 3.

Crawford-Miksza, L.K., et al., "Adenovirus Serotype Evolution is Driven by Illegitimate Recombination in the Hypervariable Regions of the Hexon Protein", "Virology", Aug. 7, 1996, pp. 357-367, vol. 224, No. 0543.

Dennis, M.S., et al., "Albumin Binding as a General Strategy for Improving the Pharmacokinetics of Proteins", "The Journal of Biological Chemistry", Sep. 20, 2002, pp. 35035-35043, vol. 277, No. 38.

Dorsett, Y., et al., "siRNAs: Applications in Functional Genomics and Potential as Therapeutics", "Nature Reviews", Apr. 2004, pp. 318-329, vol. 3.

Genbank, "hexon [Human Adenovirus 5]", "GenBank:AA024099. 1", Aug. 1, 2017.

GenBank, "hexon [Human Adenovirus 5]", "GenBank: BAG48782. 1", Jun. 14, 2008.

Giminez-Alejandre, M., et al., "Coagulation Factors Determine Tumor Transduction In Vivo", "Human Gene Therapy", Dec. 2008, pp. 1415-1419, vol. 19.

Graham, F.L., et al., "Manipulation of Adenovirus Vectors", "Methods in Molecular Biology, vol. 7: Gene Transfer and Expression Protocols", 1991, pp. 109-128.

Hearing, P., et al., "Identification of a Repeated Sequence Element Required for Efficient Encapsidation of the Adenovirus Type 5 Chromosome", "Journal of Virology", Aug. 1987, pp. 2555-2558, vol. 61, No. 8.

Hedley, S.J., et al., "Assessment of Genetic Shielding for Adenovirus Vectors", "The Open Gene Therapy Journal", 2009, pp. 1-11, vol. 2.

Johansson, M.U., et al., "Structure, Specificity, and Mode of Interaction for Bacterial Albumin-binding Modules", "The Journal of Biological Chemistry", Mar. 8, 2002, pp. 8114-8120, vol. 277, No. 10.

Jonsson, A., et al., "Engineering of a femtomolar affinity binding protein to human serum albumin", "Protein Engineering, Design & Selection", May 22, 2008, pp. 515-527, vol. 21, No. 8.

Khare, R., et al., "Identification of Adenovirus Serotype 5 Hexon Regions That Interact With Scavenger Receptors", "Journal of Virology", Feb. 2012, pp. 2293-2301, vol. 86, No. 4.

Khare, R., et al., "Circulating Antibodies and Macrophages as Modulators of Adenovirus Pharmacology", "Journal of Virology", Apr. 2013, pp. 3678-3686, vol. 87, No. 7.

Konig, T., et al., "Use of an albumin-binding domain for the selective immobilisation of recombinant capture antibody fragments on ELISA plates", "Journal of Immunological Methods", Jun. 8, 1998, pp. 73-83, vol. 218.

Kratz, F., "Albumin as a drug carrier: Design of prodrugs, drug conjugates and nanoparticles", "Journal of Controlled Release", May 17, 2008, pp. 171-183, vol. 132.

Kraulis, P.J., et al., "The serum albumin-binding domain of streptococcal protein G is a three-helical bundle: a heteronuclear NMR study", "FEBS Letters", 1996, pp. 190-194, vol. 378.

Lejon, S., et al., "Crystal Structure and Biological Implications of a Bacterial Albumin Binding Module in Complex with Human Serum Albumin", "The Journal of Bacterial Chemistry", Oct. 8, 2004, pp. 42924-42928, vol. 279, No. 41.

Linhult, M., et al., "Mutational analysis of the interaction between albumin-binding domain from streptococcal protein G and human serum albumin", "Protein Science", 2002, pp. 206-213, vol. 11.

Mackensen, A., et al., "Immunostimulatory Cytokines in Somatic Cells and Gene Therapy of Cancer", "Cytokine & Growth Factor Reviews", 1997, pp. 119-128, vol. 8, No. 2.

Martin, K., et al., "Simultaneous CAR- and aV Integrin-Binding Ablation Fails to Reduce Ad5 Liver Tropism", "Molecular Therapy", Sep. 2003, pp. 485-494, vol. 8, No. 3.

Matthews, Q.L., et al., "Optimization of capsid-incorporated antigens for a novel adenovirus vaccine approach", "Virology Journal", Aug. 21, 2008, pp. 1-13, vol. 5, No. 98.

Matthews, Q.L., "Capsid-Incorporation of Antigens into Adenovirus Capsid Proteins for a Vaccine Approach", "Molecular Pharmacology", Feb. 7, 2011, pp. 3-11, vol. 8, No. 1.

Muller, K.M., et al., "Protein Fusions to Coiled-Coil Domains", "Methods in Enzymology", 2000, pp. 261-282, vol. 328.

Nilvebrant, J., et al., "Engineering Bispecificity into a Single Albumin-Binding Domain", "PLoS ONE", Oct. 3, 2011, pp. 1-13, Article No. e25791. vol. 6, No. 10.

Noureddini, S., et al., "Genetic Targeting Strategies for Adenovirus", "Molecular Pharmaceutics", 2005, pp. 341-347, vol. 2, No. 5.

Pesonen, S., et al., "Oncolytic Adenoviruses for the Treatment of Human Cancer: Focus on Translational and Clinical Data", "Molecular Pharmaceutics", Dec. 2, 2010, pp. 12-28, vol. 8, No. 1.

Ranki, T., et al., "Serotype Chimeric Human Adenoviruses for Cancer Gene Therapy", "Viruses", 2010, pp. 2196-2212, vol. 2.

Rea, D., et al., "Highly Efficient Transduction of Human Monocyte-Derived Dendritic Cells with Subgroup B Fiber-Modified Adenovirus Vectors Enhances Transgene-Encoded Antigen Presentation to Cytotoxic T Cells", "Journal of Immunology", 2001, pp. 5236-5244.

Reddy Chichili, V.P., et al., "Linkers in the structural biology of protein-protein interactions", "Protein Science", Dec. 6, 2012, pp. 153-167, vol. 22.

Reid, T., et al., "Hepatic Arterial Infusion of a Replication-selective Oncolytic Adenovirus (dl1520): Phase II Viral, Immunologic, and Clinical Endpoints", "Cancer Research", Nov. 1, 2002, pp. 6070-6079, vol. 62.

Roberts, D.M., et al., "Hexon-chimaeric adenovirus serotype 5 vectors circumvent pre-existing anti-vector immunity", "Nature", May 11, 2006, pp. 239-243, vol. 44.

Rogozhin, V. N., et al., "An Efficient Method for the Delivery of the Interleukin-2 Gene to Human Hematopoietic Cells Using the Fiber-Modified Recombinant Adenovirus", "ACTA Nature", 2011, pp. 100-106, vol. 3, No. 10.

Rojas, J.J., et al., "Minimal RB-responsive E1A Promoter Modification to Attain Potency, Selectivity, and Transgene-arming Capacity in Oncolytic Adenoviruses", "Molecular Therapy", Nov. 2010, pp. 1960-1971, vol. 18, No. 11.

Rojas, L.A., et al., "Insertion of an albumin-binding domain in adenovirus hexon improves the pharmacokinetics and antitumor efficacy of oncolytic adenoviruses", "Human Gene Therapy", Nov. 11, 2014, p. A48, XP055199086, DOI: DOI: 10.1089/hum.2014. 2536.abstracts, vol. 25, No. 11.

Rux, J.J., et al., "Type-Specific Epitope Locations Revealed by X-Ray Crystallographic Study of Adenovirus Type 5 Hexon", "Molecular Therapy", 2000, pp. 18-30, vol. 1, No. 1.

Rux, J.J., et al., "Structural and Phylogenetic Analysis of Adenovirus Hexons by Use of High-Resolution X-Ray Crystallographic, Molecular Modeling, and Sequence-Based Methods", "Journal of Virology", Sep. 2003, pp. 9553-9566, vol. 77, No. 17.

(56) References Cited

OTHER PUBLICATIONS

Shayakhmetov, D., et al., "Efficient Gene Transfer into Human CD34+ Cells by a Retargeted Adenovirus Vector", "Journal of Virology", Mar. 2000, pp. 2567-2583.
Shimony, N., et al., "Analysis of adenoviral attachment to human platelets", "Virology Journal", Feb. 17, 2009, pp. 1-13, doi: 10.1186/1743-422X-6-25, vol. 6, No. 25.
Shiratsuchi, T., et al., "Replacing adenoviral vector HVR1 with a malaria B cell epitope improves immunogenicity and circumvents preexisting immunity to adenovirus in mice", "The Journal of Clinical Investigation", Oct. 2010, pp. 3688-3701, vol. 120, No. 10.
Stanton, R.J., et al., "Re-engineering adenovirus vector systems to enable high-throughput analyses of gene function", "BioTechniques", Dec. 2008, pp. 659-668, vol. 45.
Stevenson, S. C., et al., "Selective Targeting of Human Cells by a Chimeric Adenovirus Vector Containing a Modified Fiber Protein", "Journal of Virology", Jun. 1997, pp. 4782-4790.
Stow, N.D, et al., "The infectivity of adenovirus genomes lacking DNA sequences from their left-hand termini", "Nucleic Acids Research", Aug. 14, 1982, pp. 5105-5119, vol. 10, No. 17.
Sumida, S.M., et al., "Neutralizing Antibodies to Adenovirus Serotype 5 Vaccine Vectors Are Directed Primarily against the Adenovirus Hexon Protein", "The Journal of Immunology", Jun. 1, 2005, pp. 7179-7185, vol. 174, No. 11.
Svyatchenko, V.A., et al., "Oncolytic Adenoviruses in Anti-Cancer Therapy: Current Status and Perspectives", "Mol Biol", 2012, pp. 556-569 with Abstract, vol. 46, No. 4.
Ternovoy, V.A., et al., "The Construction of Recombinant Adenoviruses Expressing Apoptin", "Tomsk State University Journal of Biology", 2013, pp. 100-110 with Abstract, vol. 3, No. 23.
Tian, X., et al., "Protection Against Enterovirus 71 with Neutralizing Epitope Incorporation within Adenovirus Type 3 Hexon", "PLoS One", Jul. 2012, pp. e41381: 1-15, vol. 7, No. 7.
Waddington, S.N., et al., "Adenovirus Serotype 5 Hexon Mediates Liver Gene Transfer", "Cell", Feb. 8, 2008, pp. 397-409, vol. 132.
Wu, H., et al., "Identification of Sites in Adenovirus Hexon for Foreign Peptide Incorporation", "Journal of Virology", Mar. 2005, pp. 3382-3390, vol. 79, No. 6.
Xu, Z., et al., "Coagulation factor X shields adenovirus type 5 from attack by natural antibodies and complement", "Nature Medicine", Mar. 24, 2013, pp. 452-459, vol. 19, No. 4.
Alemany, "Oncolytic Adenoviruses in Cancer Treatment," Biomedicines, vol. 2, pp. 36-49, 2014.
Barouch, et al., "International Seroepidemiology of Adenovirus Serotypes 5, 26, 35, and 48 in Pediatric and Adult Populations," Vaccine, vol. 29, No. 32, pp. 5203-5209, 2011.
Cascalló, et al., "Ras-dependent Oncolysis with an Adenovirus VAI Mutant," Cancer Research, vol. 63, pp. 5544-5550, Sep. 1, 2003.
Everts, et al., "Replication-selective oncolytic viruses in the treatment of cancer," Cancer Gene Therapy, vol. 12, pp. 141-161, 2005.
Genbank: BAG48782.1 entry dated Jun. 14, 2008.
Kirn, et al., "Replication-selective oncolytic adenoviruses: virotherapy aimed at genetic targets in cancer," Oncogene, vol. 19, pp. 6660-6669, 2000.
Kurachi, et al., "Characterization of capsid-modified adenovirus vectors containing heterologous peptides in the fiber knob, protein IX, or hexon," Gene Therapy, vol. 14, pp. 266-274, 2007.
Mato-Berciano, et al., "Oncolytic adenovirus with hyaluronidase activity that evades neutralizing antibodies: VCN-11," Journal of Controlled Release, vol. 332, pp. 517-528, 2021.
Moffatt, et al., "Circumvention of Vector-Specific Neutralizing Antibody Response by Alternating Use of Human and Non-Human Adenoviruses: Implications in Gene Therapy," Virology, vol. 272, pp. 159-167, 2000.
Nattress, et al., "Advances in Oncolytic Adenovirus Therapy for Pancreatic Cancer," Cancer Letters, doi: 10.1016/j.canlet.2018.07.006, 43 pages, 2018.
Rojas, et al., "Albumin-binding adenoviruses circumvent pre-existing neutralizing antibodies upon systemic delivery," Journal of Controlled Release, vol. 237, pp. 78-88, 2016.
Uusi-Kerttula, et al., "Oncolytic Adenovirus: Strategies and Insights for Vector Design and Immuno-Oncolytic Applications," Viruses, vol. 7, pp. 6009-6042, 2015.
Wu, et al., "Construction and Characterization of Adenovirus Serotype 5 Packaged by Serotype 3 Hexon," Journal of Virology, vol. 76, No. 24, pp. 12775-12782, 2002.

SEQUENCE LISTING

```
<160> NUMBER OF SEQ ID NOS: 27

<210> SEQ ID NO 1
<211> LENGTH: 36
<212> TYPE: PRT
<213> ORGANISM: Streptococcus

<400> SEQUENCE: 1

Cys Glu Trp Asp Glu Ala Ala Thr Ala Leu Glu Ile Asn Leu Glu Glu
1               5                   10                  15

Glu Asp Asp Asp Asn Glu Asp Glu Val Asp Glu Gln Ala Glu Gln Gln
            20                  25                  30

Lys Thr His Val
        35

<210> SEQ ID NO 2
<211> LENGTH: 4
<212> TYPE: PRT
<213> ORGANISM: Artificial Sequence
```

```
<220> FEATURE:
<223> OTHER INFORMATION: linker

<400> SEQUENCE: 2

Gly Ser Gly Ser
1

<210> SEQ ID NO 3
<211> LENGTH: 3021
<212> TYPE: DNA
<213> ORGANISM: Artificial Sequence
<220> FEATURE:
<223> OTHER INFORMATION: Complete modified adenoviral hexon having ABD
      inserted in HVR1

<400> SEQUENCE: 3
atggctaccc cttcgatgat gccgcagtgg tcttacatgc acatctcggg ccaggacgcc      60
tcggagtacc tgagccccgg gctggtgcag tttgcccgcg ccaccgagac gtacttcagc     120
ctgaataaca gtttagaaa ccccacggtg gcgcctacgc acgacgtgac cacagaccgg      180
tcccagcgtt tgacgctgcg gttcatccct gtggaccgtg aggatactgc gtactcgtac     240
aaggcgcggt tcaccctagc tgtgggtgat aaccgtgtgc tggacatggc ttccacgtac     300
tttgacatcc gcggcgtgct ggacaggggc cctactttta agccctactc tggcactgcc     360
tacaacgccc tggctcccaa gggtgcccca atccttgcg aatgggatga agctgctact      420
gctcttgaaa taaacctaga agaagaggac ggcagcggat ccctggccga ggctaaggtg     480
cttgcgaacc gggaactaga caaatacggt gtttctgatt attacaagaa tttgattaac     540
aatgccaaaa ccgtcgaggg cgtaaaggct ctgatcgacg aaatacttgc ggccctaccc     600
gggtctggta gcgatgacaa cgaagacgaa gtagacgagc aagctgagca gcaaaaaact     660
cacgtatttg gcaggcgcc ttattctggt ataaatatta caaggagggg tattcaaata     720
ggtgtcgaag tcaaacacc taaatatgcc gataaaacat tcaacctga acctcaaata     780 ggagaatctc agtggtacga acagaaatt aatcatgcag ctgggagagt cctaaaaaag     840
actaccccaa tgaaaccatg ttacggttca tatgcaaaac ccacaaatga aatggaggg     900 caaggcattc ttgtaaagca acaaaatgga agctagaaa gtcaagtgga atgcaatttt     960
ttctcaacta ctgaggcagc cgcaggcaat ggtgataact tgactcctaa agtggtattg    1020
tacagtgaag atgtagatat agaaaccccca gacactcata tttcttacat gcccactatt    1080
aaggaaggta actcacgaga actaatgggc caacaatcta tgcccaacag gcctaattac    1140
attgctttta gggacaattt tattggtcta atgtattaca acagcacggg taatatgggt    1200
gttctggcgg ccaagcatc gcagttgaat gctgttgtag attgcaaga cagaaacaca    1260 gagctttcat ccagctttt gcttgattcc attggtgata accaggta cttttctatg    1320 tggaatcagg ctgttgacag ctatgatcca gatgttagaa ttattgaaaa tcatggaact    1380
gaagatgaac ttccaaatta ctgctttcca ctggaggtg tgattaatac agagactctt    1440
accaaggtaa aactaaaac aggtcaggaa aatggatggg aaaagatgc tacagaattt    1500 tcagataaa atgaataag agttggaaat aattttgcca tggaaatcaa tctaaatgcc    1560
aacctgtgga gaaatttcct gtactccaac atagcgctgt atttgcccga caagctaaag    1620
tacagtcctt ccaacgtaaa aatttctgat aacccaaaca cctacgacta catgaacaag    1680
cgagtggtgg ctcccgggct agtggactgc tacattaacc ttggagcacg ctggtcccctt    1740 gactatatgg acaacgtcaa cccatttaac caccaccgca atgctggcct gcgctaccgc    1800
```

```
tcaatgttgc tgggcaatgg tcgctatgtg cccttccaca tccaggtgcc tcagaagttc    1860
tttgccatta aaaacctcct tctcctgccg ggctcataca cctacgagtg aacttcagg     1920 aaggatgtta acatggttct gcagagctcc ctaggaaatg acctaagggt tgacggagcc    1980
agcattaagt ttgatagcat ttgcctttac gccaccttct tccccatggc ccacaacacc    2040
gcctccacgc ttgaggccat gcttagaaac gacaccaacg accagtcctt taacgactat    2100
ctctccgccg ccaacatgct ctaccctata cccgccaacg ctaccaacgt gcccatatcc    2160
atcccctccc gcaactgggc ggcttccgc ggctgggcct tcacgcgcct taagactaag     2220
gaaaccccat cactgggctc gggctacgac ccttattaca cctactctgg ctctataccc    2280
tacctagatg aaccttta cctcaaccac acctttaaga aggtggccat tacctttgac      2340
tcttctgtca gctggcctgg caatgaccgc ctgcttaccc caacgagtt tgaaattaag     2400 cgctcagttg acggggaggg ttacaacgtt gcccagtgta acatgaccaa agactggttc    2460
ctggtacaaa tgctagctaa ctataacatt ggctaccagg gcttctatat cccagagagc    2520
tacaaggacc gcatgtactc cttctttaga aacttccagc ccatgagccg tcaggtggtg    2580
gatgatacta atacaagga ctaccaacag gtgggcatcc tacaccaaca caacaactct     2640
ggatttgttg gctaccttgc ccccaccatg cgcgaaggac aggcctaccc tgctaacttc    2700
ccctatccgc ttataggcaa gaccgcagtt gacagcatta cccagaaaaa gtttctttgc    2760
gatcgcaccc tttggcgcat cccattctcc agtaacttta tgtccatggg cgcactcaca    2820
gacctgggcc aaaaccttct ctacgccaac tccgcccacg cgctagacat gacttttgag    2880
gtggatccca tggacgagcc caccttcttc tatgttttgt ttgaagtctt tgacgtggtc    2940
cgtgtgcacc agccgcaccg cggcgtcatc gaaaccgtgt acctgcgcac gcccttctcg    3000
gccggcaacg ccacaacata a                                              3021
```

<210> SEQ ID NO 4
<211> LENGTH: 3021
<212> TYPE: DNA
<213> ORGANISM: Artificial Sequence
<220> FEATURE:
<223> OTHER INFORMATION: Complete modified adenoviral hexon having ABD
      inserted in HVR5

<400> SEQUENCE: 4

```
atggctaccc cttcgatgat gccgcagtgg tcttacatgc acatctcggg ccaggacgcc     60
tcggagtacc tgagccccgg gctggtgcag tttgcccgcg ccaccgagac gtacttcagc    120
ctgaataaca gtttagaaa ccccacggtg gcgcctacgc acgacgtgac cacagaccgg     180
tcccagcgtt tgacgctgcg gttcatccct gtggaccgtg aggatactgc gtactcgtac    240
aaggcgcggt tcaccctagc tgtgggtgat aaccgtgtgc tggacatggc ttccacgtac    300
tttgacatcc gcggcgtgct ggacaggggc cctactttta gccctactc tggcactgcc    360 tacaacgccc tggctcccaa gggtgcccca atccttgcg aatgggatga agctgctact     420
gctcttgaaa taaacctaga agaagaggac gatgacaacg aagacgaagt agacgagcaa    480
gctgagcagc aaaaaactca cgtatttggg caggcgcctt attctggtat aaatattaca    540
aaggagggta ttcaataggg tgtcgaaggt caaacaccta aatatgccga taaaacattt    600
caacctgaac ctcaaatagg agaatctcag tggtacgaaa cagaaattaa tcatgcagct    660
gggagagtcc taaaaaagac taccccaatg aaaccatgtt acggttcata tgcaaacccc    720
acaaatgaaa atggagggca aggcattctt gtaaagcaac aaaatggaaa gctagaaagt    780
```

```
caagtggaaa tgcaattttt ctcaactact gaggcagccg caggcagcgg atccctggcc      840
gaggctaagg tgcttgcgaa ccgggaacta gacaaatacg gtgtttctga ttattacaag      900
aatttgatta acaatgccaa aaccgtcgag ggcgtaaagg ctctgatcga cgaaatactt      960
gcggccctac ccgggtctgg tagcggcaat ggtgataact tgactcctaa agtggtattg     1020
tacagtgaag atgtagatat agaaacccca gacactcata tttcttacat gcccactatt     1080
aaggaaggta actcacgaga actaatgggc caacaatcta tgcccaacag gcctaattac     1140
attgctttta gggacaattt tattggtcta atgtattaca acagcacggg taatatgggt     1200
gttctggcgg gccaagcatc gcagttgaat gctgttgtag atttgcaaga cagaaacaca     1260
gagctttcat accagctttt gcttgattcc attggtgata gaaccaggta cttttctatg     1320
tggaatcagg ctgttgacag ctatgatcca gatgttagaa ttattgaaaa tcatggaact     1380
gaagatgaac ttccaaatta ctgctttcca ctgggaggtg tgattaatac agagactctt     1440
accaaggtaa aacctaaaac aggtcaggaa aatggatggg aaaaagatgc tacagaattt     1500
tcagataaaa atgaaataag agttggaaat aattttgcca tggaaatcaa tctaaatgcc     1560
aacctgtgga gaaatttcct gtactccaac atagcgctgt atttgcccga caagctaaag     1620
tacagtcctt ccaacgtaaa aatttctgat aacccaaaca cctacgacta catgaacaag     1680
cgagtggtgg ctcccgggct agtggactgc tacattaacc ttggagcacg ctggtccctt     1740
gactatatgg acaacgtcaa cccatttaac caccaccgca atgctggcct gcgctaccgc     1800
tcaatgttgc tgggcaatgg tcgctatgtg cccttccaca tccaggtgcc tcagaagttc     1860
tttgccatta aaaacctcct tctcctgccg ggctcataca cctacgagtg gaacttcagg     1920
aaggatgtta acatggttct gcagagctcc ctaggaaatg acctaagggt tgacggagcc     1980
agcattaagt ttgatagcat ttgccttta c gccaccttct tccccatggc ccacaacacc     2040
gcctccacgc ttgaggccat gcttagaaac gacaccaacg accagtcctt taacgactat     2100
ctctccgccg ccaacatgct ctaccctata cccgccaacg ctaccaacgt gcccatatcc     2160 atccctccc gcaactgggc ggctttccgc ggctgggcct tcacgcgcct taagactaag     2220
gaaaccccat cactgggctc gggctacgac ccttattaca cctactctgg ctctataccc     2280
tacctagatg gaaccttta cctcaaccac acctttaaga aggtggccat taccctttgac     2340 tcttctgtca gctggcctgg caatgaccgc ctgcttaccc caacgagtt tgaaattaag     2400 cgctcagttg acggggaggg ttacaacgtt gcccagtgta acatgaccaa agactggttc     2460
ctggtacaaa tgctagctaa ctataacatt ggctaccagg gcttctatat cccagagagc     2520
tacaaggacc gcatgtactc cttctttaga aacttccagc ccatgagccg tcaggtggtg     2580
gatgatacta aatacaagga ctaccaacag gtgggcatcc tacaccaaca caacaactct     2640
ggatttgttg gctaccttgc ccccaccatg cgcgaaggac aggcctaccc tgctaacttc     2700
ccctatccgc ttataggcaa gaccgcagtt gacagcatta cccagaaaaa gtttctttgc     2760
gatcgcaccc tttggcgcat cccattctcc agtaacttta tgtccatggg cgcactcaca     2820
gacctgggcc aaaaccttct ctacgccaac tccgcccacg cgctagacat gacttttgag     2880
gtggatccca tggacgagcc cacccttctt tatgttttgt ttgaagtctt tgacgtggtc     2940
cgtgtgcacc agccgcaccg cggcgtcatc gaaaccgtgt acctgcgcac gcccttctcg     3000
gccggcaacg ccacaacata a                                               3021
```

```
<210> SEQ ID NO 5
<211> LENGTH: 14
<212> TYPE: PRT
<213> ORGANISM: Artificial Sequence
<220> FEATURE:
<223> OTHER INFORMATION: linker

<400> SEQUENCE: 5

Ser Gly Gly Thr Ser Gly Ser Thr Ser Gly Thr Gly Ser Thr
1               5                   10

<210> SEQ ID NO 6
<211> LENGTH: 15
<212> TYPE: PRT
<213> ORGANISM: Artificial Sequence
<220> FEATURE:
<223> OTHER INFORMATION: linker

<400> SEQUENCE: 6

Ala Gly Ser Ser Thr Gly Ser Ser Thr Gly Pro Gly Ser Thr Thr
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: linker

<400> SEQUENCE: 7

Gly Gly Ser Gly Gly Ala Pro
1               5

<210> SEQ ID NO 8
<211> LENGTH: 8
<212> TYPE: PRT
<213> ORGANISM: Artificial Sequence
<220> FEATURE:
<223> OTHER INFORMATION: linker

<400> SEQUENCE: 8

Gly Gly Gly Val Glu Gly Gly Gly
1               5

<210> SEQ ID NO 9
<211> LENGTH: 11
<212> TYPE: PRT
<213> ORGANISM: Artificial Sequence
<220> FEATURE:
<223> OTHER INFORMATION: Core sequence of an albumin-binding peptide

<400> SEQUENCE: 9

Asp Ile Cys Leu Pro Arg Trp Gly Cys Leu Trp
1               5                   10

<210> SEQ ID NO 10
<211> LENGTH: 4
<212> TYPE: PRT
<213> ORGANISM: Human adenovirus type 5

<400> SEQUENCE: 10

Lys Lys Thr Lys
1
```

```
<210> SEQ ID NO 11
<211> LENGTH: 4
<212> TYPE: PRT
<213> ORGANISM: Artificial Sequence
<220> FEATURE:
<223> OTHER INFORMATION: modified capsid domain

<400> SEQUENCE: 11

Arg Gly Asp Lys
1

<210> SEQ ID NO 12
<211> LENGTH: 56
<212> TYPE: DNA
<213> ORGANISM: Artificial Sequence
<220> FEATURE:
<223> OTHER INFORMATION: oligonucleotide HVR1rpsLF

<400> SEQUENCE: 12
gccctggctc ccaagggtgc cccaaatcct tgcgaatggg gcctggtgat gatggc        56

<210> SEQ ID NO 13
<211> LENGTH: 65
<212> TYPE: DNA
<213> ORGANISM: Artificial Sequence
<220> FEATURE:
<223> OTHER INFORMATION: oligonucleotide HVR1rpsLR

<400> SEQUENCE: 13
gtaatattta taccagaata aggcgcctgc ccaaatacgt gagttcagaa gaactcgtca    60
agaag                                                                65

<210> SEQ ID NO 14
<211> LENGTH: 90
<212> TYPE: DNA
<213> ORGANISM: Artificial Sequence
<220> FEATURE:
<223> OTHER INFORMATION: oligonucleotide ABDH1F

<400> SEQUENCE: 14
cccaagggtg ccccaaatcc ttgcgaatgg gatgaagctg ctactgctct tgaaataaac    60
ctagaagaag aggacggcag cggatccctg                                      90

<210> SEQ ID NO 15
<211> LENGTH: 49
<212> TYPE: DNA
<213> ORGANISM: Artificial Sequence
<220> FEATURE:
<223> OTHER INFORMATION: oligonucleotide ABDR1

<400> SEQUENCE: 15
cccggttcgc aagcacctta gcctcggcca gggatccgct gccccattc                 49

<210> SEQ ID NO 16
<211> LENGTH: 49
<212> TYPE: DNA
<213> ORGANISM: Artificial Sequence
<220> FEATURE:
<223> OTHER INFORMATION: oligonucleotide ABDF2

<400> SEQUENCE: 16
gcttgcgaac cgggaactag acaaatacgg tgtttctgat tattacaag                 49
```

```
<210> SEQ ID NO 17
<211> LENGTH: 50
<212> TYPE: DNA
<213> ORGANISM: Artificial Sequence
<220> FEATURE:
<223> OTHER INFORMATION: oligonucleotide ABDR2

<400> SEQUENCE: 17
cgacggtttt ggcattgtta atcaaattct tgtaataatc agaaacaccg            50

<210> SEQ ID NO 18
<211> LENGTH: 50
<212> TYPE: DNA
<213> ORGANISM: Artificial Sequence
<220> FEATURE:
<223> OTHER INFORMATION: oligonucleotide ABDF3

<400> SEQUENCE: 18
atgccaaaac cgtcgagggc gtaaaggctc tgatcgacga atacttgcg             50

<210> SEQ ID NO 19
<211> LENGTH: 50
<212> TYPE: DNA
<213> ORGANISM: Artificial Sequence
<220> FEATURE:
<223> OTHER INFORMATION: oligonucleotide ABDR3

<400> SEQUENCE: 19
atacgtgagt gctaccagac ccgggtaggg ccgcaagtat ttcgtcgatc            50

<210> SEQ ID NO 20
<211> LENGTH: 91
<212> TYPE: DNA
<213> ORGANISM: Artificial Sequence
<220> FEATURE:
<223> OTHER INFORMATION: oligonucleotide ABDH1R

<400> SEQUENCE: 20
cagaataagg cgcctgccca aatacgtgag ttttttgctg ctcagcttgc tcgtctactt    60
cgtcttcgtt gtcatcgcta ccagacccgg g                                 91

<210> SEQ ID NO 21
<211> LENGTH: 58
<212> TYPE: DNA
<213> ORGANISM: Artificial Sequence
<220> FEATURE:
<223> OTHER INFORMATION: oligonucleotide H5rpsLF

<400> SEQUENCE: 21
gaaagctaga aagtcaagtg gaaatgcaat ttttctcaac tggcctggtg atgatggc      58

<210> SEQ ID NO 22
<211> LENGTH: 62
<212> TYPE: DNA
<213> ORGANISM: Artificial Sequence
<220> FEATURE:
<223> OTHER INFORMATION: oligonucleotide H5rpsLR

<400> SEQUENCE: 22
gtttctatat ctacatcttc actgtacaat accactttag gtcagaagaa ctcgtcaaga    60
ag                                                                  62
```

```
<210> SEQ ID NO 23
<211> LENGTH: 138
<212> TYPE: DNA
<213> ORGANISM: Artificial Sequence
<220> FEATURE:
<223> OTHER INFORMATION: oligonucleotide ABDH5F

<400> SEQUENCE: 23
ctggccgagg ctaaggtgct tgcgaaccgg gaactagaca aatacggtgt ttctgattat      60
tacaagaatt tgattaacaa tgccaaaacc gtcgagggcg taaaggctct gatcgacgaa     120
atacttgcgg ccctaccc                                                    138

<210> SEQ ID NO 24
<211> LENGTH: 138
<212> TYPE: DNA
<213> ORGANISM: Artificial Sequence
<220> FEATURE:
<223> OTHER INFORMATION: oligonucleotide ABDH5R

<400> SEQUENCE: 24
ctggccgagg ctaaggtgct tgcgaaccgg gaactagaca aatacggtgt ttctgattat      60
tacaagaatt tgattaacaa tgccaaaacc gtcgagggcg taaaggctct gatcgacgaa     120
atacttgcgg ccctaccc                                                    138

<210> SEQ ID NO 25
<211> LENGTH: 20
<212> TYPE: DNA
<213> ORGANISM: Artificial Sequence
<220> FEATURE:
<223> OTHER INFORMATION: oligonucleotide Ad19121F

<400> SEQUENCE: 25
ctggacatgg cttccacgta                                                   20

<210> SEQ ID NO 26
<211> LENGTH: 20
<212> TYPE: DNA
<213> ORGANISM: Artificial Sequence
<220> FEATURE:
<223> OTHER INFORMATION: oligonucleotide Ad19300R

<400> SEQUENCE: 26
gctcgtctac ttcgtcttcg                                                   20

<210> SEQ ID NO 27
<211> LENGTH: 952
<212> TYPE: PRT
<213> ORGANISM: Human adenovirus type 5

<400> SEQUENCE: 27
```

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
                20                  25                  30

Arg Ala Thr Glu Thr Tyr Phe Ser Leu Asn Asn Lys Phe Arg Asn Pro
            35                  40                  45

Thr Val Ala Pro Thr His Asp Val Thr Thr Asp Arg Ser Gln Arg Leu
        50                  55                  60

Thr Leu Arg Phe Ile Pro Val Asp Arg Glu Asp Thr Ala Tyr Ser Tyr
65                  70                  75                  80

-continued

```
Lys Ala Arg Phe Thr Leu Ala Val Gly Asp Asn Arg Val Leu Asp Met
                 85                  90                  95
Ala Ser Thr Tyr Phe Asp Ile Arg Gly Val Leu Asp Arg Gly Pro Thr
            100                 105                 110
Phe Lys Pro Tyr Ser Gly Thr Ala Tyr Asn Ala Leu Ala Pro Lys Gly
        115                 120                 125
Ala Pro Asn Pro Cys Glu Trp Asp Glu Ala Ala Thr Ala Leu Glu Ile
    130                 135                 140
Asn Leu Glu Glu Glu Asp Asp Asn Glu Asp Glu Val Asp Glu Gln
145                 150                 155                 160
Ala Glu Gln Gln Lys Thr His Val Phe Gly Gln Ala Pro Tyr Ser Gly
                165                 170                 175
Ile Asn Ile Thr Lys Glu Gly Ile Gln Ile Gly Val Glu Gly Gln Thr
            180                 185                 190
Pro Lys Tyr Ala Asp Lys Thr Phe Gln Pro Glu Pro Gln Ile Gly Glu
        195                 200                 205
Ser Gln Trp Tyr Glu Thr Glu Ile Asn His Ala Ala Gly Arg Val Leu
    210                 215                 220
Lys Lys Thr Thr Pro Met Lys Pro Cys Tyr Gly Ser Tyr Ala Lys Pro
225                 230                 235                 240
Thr Asn Glu Asn Gly Gly Gln Gly Ile Leu Val Lys Gln Gln Asn Gly
                245                 250                 255
Lys Leu Glu Ser Gln Val Glu Met Gln Phe Phe Ser Thr Glu Ala
            260                 265                 270
Ala Ala Gly Asn Gly Asp Asn Leu Thr Pro Lys Val Val Leu Tyr Ser
        275                 280                 285
Glu Asp Val Asp Ile Glu Thr Pro Asp Thr His Ile Ser Tyr Met Pro
    290                 295                 300
Thr Ile Lys Glu Gly Asn Ser Arg Glu Leu Met Gly Gln Gln Ser Met
305                 310                 315                 320
Pro Asn Arg Pro Asn Tyr Ile Ala Phe Arg Asp Asn Phe Ile Gly Leu
                325                 330                 335
Met Tyr Tyr Asn Ser Thr Gly Asn Met Gly Val Leu Ala Gly Gln Ala
            340                 345                 350
Ser Gln Leu Asn Ala Val Val Asp Leu Gln Asp Arg Asn Thr Glu Leu
        355                 360                 365
Ser Tyr Gln Leu Leu Leu Asp Ser Ile Gly Asp Arg Thr Arg Tyr Phe
    370                 375                 380
Ser Met Trp Asn Gln Ala Val Asp Ser Tyr Asp Pro Asp Val Arg Ile
385                 390                 395                 400
Ile Glu Asn His Gly Thr Glu Asp Glu Leu Pro Asn Tyr Cys Phe Pro
                405                 410                 415
Leu Gly Gly Val Ile Asn Thr Glu Thr Leu Thr Lys Val Lys Pro Lys
            420                 425                 430
Thr Gly Gln Glu Asn Gly Trp Glu Lys Asp Ala Thr Glu Phe Ser Asp
        435                 440                 445
Lys Asn Glu Ile Arg Val Gly Asn Asn Phe Ala Met Glu Ile Asn Leu
    450                 455                 460
Asn Ala Asn Leu Trp Arg Asn Phe Leu Tyr Ser Asn Ile Ala Leu Tyr
465                 470                 475                 480
Leu Pro Asp Lys Leu Lys Tyr Ser Pro Ser Asn Val Lys Ile Ser Asp
                485                 490                 495
```

-continued

```
Asn Pro Asn Thr Tyr Asp Tyr Met Asn Lys Arg Val Ala Pro Gly
            500                 505                 510

Leu Val Asp Cys Tyr Ile Asn Leu Gly Ala Arg Trp Ser Leu Asp Tyr
            515                 520                 525

Met Asp Asn Val Asn Pro Phe Asn His His Arg Asn Ala Gly Leu Arg
    530                 535                 540

Tyr Arg Ser Met Leu Leu Gly Asn Gly Arg Tyr Val Pro Phe His Ile
545                 550                 555                 560

Gln Val Pro Gln Lys Phe Phe Ala Ile Lys Asn Leu Leu Leu Pro
                565                 570                 575

Gly Ser Tyr Thr Tyr Glu Trp Asn Phe Arg Lys Asp Val Asn Met Val
                580                 585                 590

Leu Gln Ser Ser Leu Gly Asn Asp Leu Arg Val Asp Gly Ala Ser Ile
                595                 600                 605

Lys Phe Asp Ser Ile Cys Leu Tyr Ala Thr Phe Phe Pro Met Ala His
            610                 615                 620

Asn Thr Ala Ser Thr Leu Glu Ala Met Leu Arg Asn Asp Thr Asn Asp
625                 630                 635                 640

Gln Ser Phe Asn Asp Tyr Leu Ser Ala Ala Asn Met Leu Tyr Pro Ile
                645                 650                 655

Pro Ala Asn Ala Thr Asn Val Pro Ile Ser Ile Pro Ser Arg Asn Trp
                660                 665                 670

Ala Ala Phe Arg Gly Trp Ala Phe Thr Arg Leu Lys Thr Lys Glu Thr
                675                 680                 685

Pro Ser Leu Gly Ser Gly Tyr Asp Pro Tyr Tyr Thr Tyr Ser Gly Ser
        690                 695                 700

Ile Pro Tyr Leu Asp Gly Thr Phe Tyr Leu Asn His Thr Phe Lys Lys
705                 710                 715                 720

Val Ala Ile Thr Phe Asp Ser Ser Val Ser Trp Pro Gly Asn Asp Arg
                725                 730                 735

Leu Leu Thr Pro Asn Glu Phe Glu Ile Lys Arg Ser Val Asp Gly Glu
                740                 745                 750

Gly Tyr Asn Val Ala Gln Cys Asn Met Thr Lys Asp Trp Phe Leu Val
        755                 760                 765

Gln Met Leu Ala Asn Tyr Asn Ile Gly Tyr Gln Gly Phe Tyr Ile Pro
770                 775                 780

Glu Ser Tyr Lys Asp Arg Met Tyr Ser Phe Phe Arg Asn Phe Gln Pro
785                 790                 795                 800

Met Ser Arg Gln Val Val Asp Asp Thr Lys Tyr Lys Asp Tyr Gln Gln
                805                 810                 815

Val Gly Ile Leu His Gln His Asn Asn Ser Gly Phe Val Gly Tyr Leu
                820                 825                 830

Ala Pro Thr Met Arg Glu Gly Gln Ala Tyr Pro Ala Asn Phe Pro Tyr
            835                 840                 845

Pro Leu Ile Gly Lys Thr Ala Val Asp Ser Ile Thr Gln Lys Lys Phe
        850                 855                 860

Leu Cys Asp Arg Thr Leu Trp Arg Ile Pro Phe Ser Ser Asn Phe Met
865                 870                 875                 880

Ser Met Gly Ala Leu Thr Asp Leu Gly Gln Asn Leu Leu Tyr Ala Asn
                885                 890                 895

Ser Ala His Ala Leu Asp Met Thr Phe Glu Val Asp Pro Met Asp Glu
            900                 905                 910
```

-continued

```
Pro Thr Leu Leu Tyr Val Leu Phe Glu Val Phe Asp Val Val Arg Val
            915                 920                 925

His Gln Pro His Arg Gly Val Ile Glu Thr Val Tyr Leu Arg Thr Pro
    930                 935                 940

Phe Ser Ala Gly Asn Ala Thr Thr
945                 950
```

ADENOVIRUS COMPRISING AN ALBUMIN-BINDING MOIETY

CROSS-REFERENCE TO RELATED APPLICATIONS

This is a continuation under 35 USC § 120 of U.S. patent application Ser. No. 15/307,408 filed Oct. 28, 2016 in the names of RAMON ALEMANY BONASTRE and LUIS ALFONSO ROJAS EXPÓSITO for ADENOVIRUS COMPRISING AN ALBUMIN-BINDING MOIETY, which in turn is a U.S. national phase application under the provisions of 35 U.S.C. § 371 of International Patent Application No. PCT/EP15/59593 filed Apr. 30, 2015, which in turn claims priority of European Patent Application No. 14382162.7 filed Apr. 30, 2014. The disclosures of U.S. patent application Ser. No. 15/307,408, International Patent Application No. PCT/EP15/59593 and European Patent Application No. 14382162.7 are hereby incorporated herein by reference in their respective entireties, for all purposes.

DESCRIPTION OF THE TEXT FILE SUBMITTED ELECTRONICALLY

The content of the text file submitted electronically herewith is incorporated herein by reference in its entirety: A computer readable format copy of the Sequence Listing (Filename: "VCN-003C1_Replacement_Sequence_Listing.txt"; Date created: Aug. 10, 2022; File size: 21.7 KB).

FIELD OF THE INVENTION

The invention relates to the field of disease therapy and, more in particular, to a recombinant adenovirus for gene therapy or virotherapy comprising an albumin-binding moiety on the outer surface of the adenoviral hexon protein, particularly to an oncolytic adenovirus comprising an albumin-binding moiety and to its use for the prevention and/or treatment of cancer. Said adenoviruses are shielded against neutralizing antibodies present in the bloodstream and are thus particularly suitable for systemic administration.

BACKGROUND OF THE INVENTION

Adenoviruses have been extensively used as gene delivery vectors for gene therapy as well as oncolytic agents for cancer treatment. They exhibit several features that make them suitable for these applications. Namely, their structure and biology has been widely studied which allows for an easy modification of their genome, they are able to infect both replicating and non-replicating cells, and they can easily be produced at high titers for their use in the clinic. In terms of safety, they do not cause life-threatening diseases in humans, and their genome is non-integrative which prevents for insertional mutagenesis. Clinical trials with adenovirus-based vectors report a good toxicology and safety profile, although the efficacy still needs improvement, especially when the virus is administered systemically.

In the field of gene therapy, systemic administration, that is, injection into the bloodstream endovenously or intra-arterially, may be needed to reach multiple organs or disseminated cells. For example, in cancer therapy with adenovirus vectors and oncolytic adenoviruses systemic administration is necessary to treat disseminated tumours at an advanced or metastatic stage. Nonetheless, adenoviruses show important limitations when injected into the bloodstream that impair the efficacy of the therapy. Adenovirus type 5 (Ad5) suffers multiple neutralizing interactions in the bloodstream that reduce drastically the bioavailability of the virus. Liver sequestration represents the major obstacle for the therapy since >90% of the injected dose is retained by this organ, mainly by liver macrophages named Kupffer cells, but also by liver sinusoidal endothelial cells (LSECs) and hepatocytes. Direct interaction with blood cells and proteins also represents an important barrier. Ad5 can bind directly to blood cells such as erythrocytes via CAR receptor and to platelets via integrins. Antibodies not only can neutralize the virus directly but can also trigger an innate immune response by complement activation and by docking the virus particles to the Fc receptors of monocytes and neutrophils. Furthermore, vector re-administration raises the levels of anti-Ad neutralizing antibodies (NAbs) and therefore the neutralization of the virus. Adenovirus opsonization by antibodies and complement also enhances clearance by Kupffer cells. Altogether, these interactions result in a very short half-life of Ad in blood, of about few minutes in mice and humans.

Extensive efforts have been made to evade the neutralization by antibodies and immune cells when the adenovirus is systemically administered.

Chemical modification of adenovirus capsid with polymers (polyethyleneglycol (PEG) or N-(2-hydroxypropyl) methacrylamide (HPMA)) has been tested. Polymer conjugation on viral surface enabled the virus to evade neutralisation by antibodies and immune cells as well as ablates CAR, integrin, and FX-binding. Nevertheless, polymers conjugated to the capsid do not pass to the virus progeny and increase the complexity of large-scale GMP production for clinical application.

WO 2011/129468 A9 discloses a chimeric adenovirus capable of evading immune recognition of neutralizing antibodies. Said adenovirus was obtained by genetic modification of the capsid of human adenovirus serotype 5, wherein the gene that codes for hexon protein was replaced by the hexon gene from simian adenovirus serotype 19. The chimeric adenovirus obtained showed also higher anti-tumour activity than the same adenovirus without the genetic modification.

Several attempts have been made in order to obtain an adenovirus shielded by albumin protein (see WO 2007/050128 A2). However, experimental evidence has demonstrated that an adenovirus having a capsid modified with an albumin-binding domain is not protected against neutralizing antibodies (Hedley S. J. et al. 2009. The Open Gene Therapy Journal, 2:1-11).

Therefore, there is still a need for further genetic modified adenovirus suitable for systemic administration and capable of escaping neutralizing antibodies.

BRIEF DESCRIPTION OF THE INVENTION

In a first aspect, the invention relates to an adenoviral genome characterized in that it comprises a sequence encoding an albumin-binding moiety inserted in the coding region of the hypervariable region 1 (HVR1) of the hexon protein which results in the expression of fusion protein comprising a hexon protein and an albumin-binding moiety and wherein the albumin-binding moiety is located on the outer surface of the hexon protein when the hexon protein is assembled in the adenovirus capsid.

In a second aspect, the invention relates to a recombinant adenovirus having an adenoviral genome according to the invention.

In a third aspect, the invention relates to a pharmaceutical composition comprising a therapeutically effective amount of a recombinant adenovirus according to the invention together with a pharmaceutically acceptable carrier.

In a fourth aspect, the invention relates to a recombinant adenovirus or a pharmaceutical composition according to the invention for use in medicine.

In a further aspect, the invention relates to a recombinant adenovirus or a pharmaceutical composition according to the invention for use in the prevention and/or treatment of cancer in a mammal, wherein the adenovirus is an oncolytic adenovirus or an adenovirus comprising a gene used in cancer therapy inserted in its genome.

BRIEF DESCRIPTION OF THE FIGURES

FIG. 5A) Wells were coated with either human or bovine serum albumin (HSA or BSA, which binds or doesn't bind to ABD, respectively). Three different amounts of viral protein were tested to detect the binding (0.25, 2.5, and 25 ng). ICOVIR15 and ICOVIR15-ABD adenoviruses binding to albumin-coated wells were detected after incubation with antihexon antibody and peroxidase-labelled secondary antibody by colorimetric analysis. Samples were evaluated in triplicate. Mean±SD error bars are plotted. OD, optical density. * Statistical significance compared to other groups (p≤0.05). FIG. 5B) Wells were coated with either bovine, human, or mouse serum albumin (BSA, HSA, or MSA). The amount of viral protein tested was 25 ng. Adenovirus binding to albumin-coated wells was detected after incubation with antihexon antibody and peroxidase-labelled secondary antibody by colorimetric analysis. A control mock group without adenovirus was included. Samples were evaluated in triplicate. Mean±SD error bars are plotted. OD, optical density. * Statistical significance compared to other groups (p≤0.05).

ABD virus. After one week the cells and supernatant were harvested and lysed by three freeze-thaw cycles. The cell extract containing virus was tittered in HEK293 cells by plaque assay. Wells corresponding to dilutions 1E6, 1E7 and 1E8 are shown, where plaques demonstrating virus propagation are evident.

Figure 12:
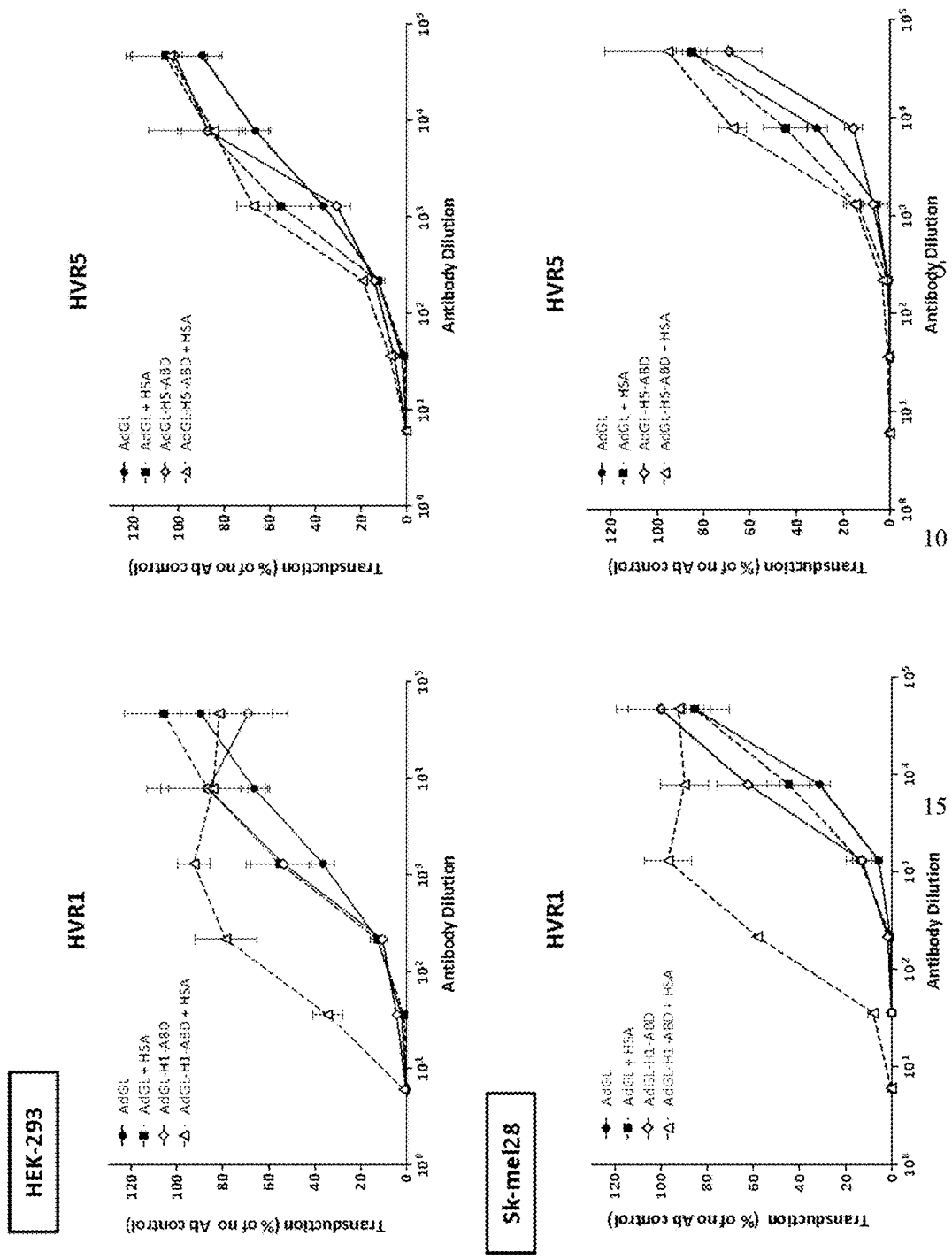

FIG. 12. Albumin-binding domain inserted in HVR5 does not protect adenovirus from neutralizing antibodies, contrary to the same domain inserted in HVR1. An in vitro neutralization experiment was performed in HEK293 and Sk-mel28 cells comparing AdGL, AdGL-H1-ABD, and AdGL-H5-ABD. Adenoviruses were incubated for 1 hour with serial dilutions of the neutralizing antibody Ab6982 in presence or absence of Human Serum Albumin (HSA). Cells were subsequently added to obtain a multiplicity of infection of 10 viral particles (vp) per cell (HEK293) and 40 vp per cell (Sk-mel28). Twenty-four hours after the infection, transduction of cells was analyzed by luciferase expression. A control without antibody (Ab) ("no Ab" control) was included to obtain the 100% infection value Samples were evaluated in triplicate. Mean±SD error bars are plotted.

DETAILED DESCRIPTION OF THE INVENTION

The inventors of the present invention have discovered that an adenovirus genetically modified with an albumin-binding moiety on the outer surface of the capsid, particularly on the outer surface of the adenoviral hexon protein, is capable of acquiring an albumin shield allowing the virus to escape neutralizing antibodies and increasing its blood persistence after systemic administration. This result is unexpected because previous attempts of modifying an adenovirus with an albumin-binding domain failed to increase protection of the adenovirus against neutralizing antibodies (Hedley S. J. et al. 2009. The Open Gene Therapy Journal, 2:1-11).

Additionally, when the recombinant adenovirus is an oncolytic adenovirus, the insertion of the albumin-binding moiety improves its anti-tumour activity. In this sense, said genetically modified adenoviruses have potential value for overcoming limitations of systemic administration, particularly for the treatment of cancer.

Figure 6:
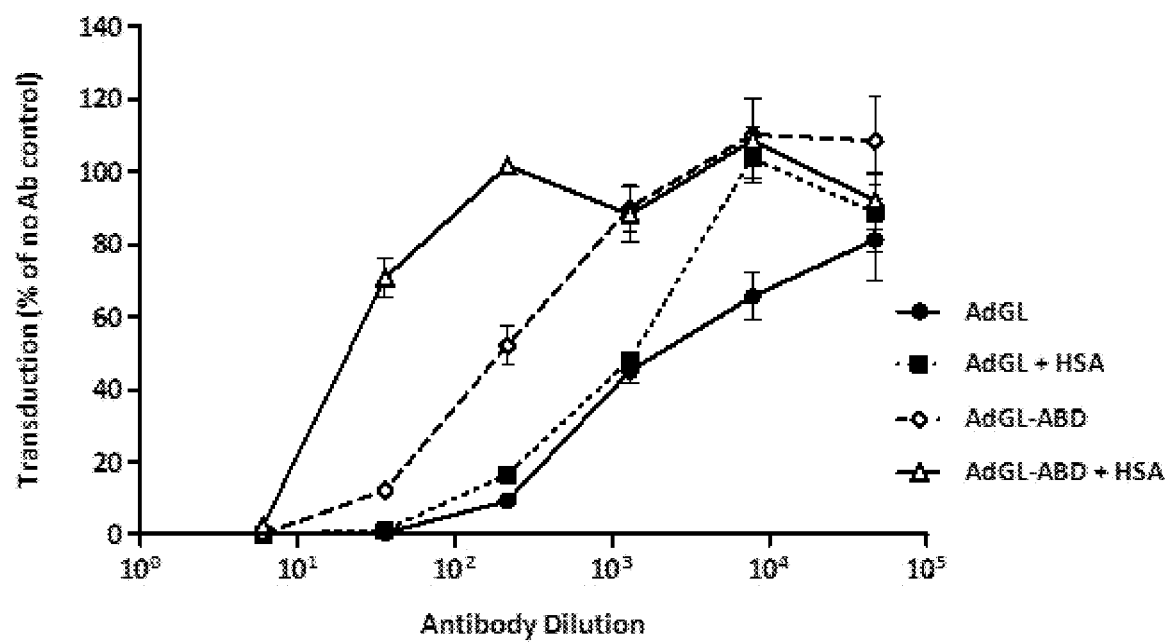
FIG. 6. Albumin-binding protects adenovirus from neutralizing antibodies in vitro. AdGL and AdGL-ABD adenoviruses coated or not with human serum albumin (HSA) were incubated with serial dilutions of the neutralizing antibody Ab6982 for 1 hour at 37° C. HEK293 cells were then added to obtain a multiplicity of infection of 0.5 transducing units (TU) per cell. 24 hours after the infection, transduction of cells was analyzed by luciferase expression. A control without antibody (Ab) ("no Ab" control) was included to obtain the 100% infection value. Samples were evaluated in triplicate. Mean±SD error bars are plotted.

The results provided in the examples of the present invention clearly show that a replication-selective oncolytic adenovirus (ICOVIR15-ABD) comprising a sequence encoding an albumin-binding domain (ABD) from streptococcal protein G inserted in the hypervariable region 1 (HVR1) of the hexon protein coding sequence, expose this domain on its capsid promoting albumin binding, shielding the adenovirus against neutralizing antibodies, increasing its plasma half-life and improving its anti-tumour efficacy. The experimental examples provided by the present invention also show that the insertion of an ABD from streptococcal protein G in the HVR1 of the hexon protein of a replication-deficient adenovirus (AdGL-ABD) protects the adenovirus from neutralizing antibodies (FIG. 6). Thus, these results show that the albumin-coating of the adenovirus acts as a shield to hide viral proteins and avoid multiple undesired interactions in blood (neutralizing antibodies, blood-cell absorption and liver uptake) improving its pharmacokinetics. This is especially important when an adenovirus vector for gene therapy, vaccine or oncolytic adenovirus is re-administered. Therefore, the genetically modified adenoviruses of the invention are suitable for systemic administration.

Adenoviruses of the Invention

The results obtained in the present invention show that an adenovirus comprising an albumin-binding moiety on the outer surface of the adenoviral hexon protein can be coated with albumin thus protecting itself from neutralizing antibodies present in the bloodstream. This protective effect is observed both for replicative (ICOVIR15-ABD) and non-replicative (AdGL-ABD) adenoviruses.

In an aspect, the invention relates to a recombinant adenovirus having an adenoviral genome characterized in that it comprises a sequence encoding an albumin-binding moiety inserted in the coding region of the hypervariable region 1 (HVR1) of the hexon protein which results in the expression of fusion protein comprising a hexon protein and an albumin-binding moiety and wherein the albumin-binding moiety is located on the outer surface of the hexon protein when the hexon protein is assembled in the adenovirus capsid.

The term "adenovirus", as used herein, refers to any virus that can be categorized as an adenovirus, i.e. any virus pertaining to the Adenoviridae family characterized by being a non-enveloped virus with an icosahedral nucleocapsid containing a double stranded DNA genome. This term includes any adenovirus capable of infecting a human or an animal, including all groups, subgroups, and serotypes that use CAR as receptor for infection of target cells. Adenoviruses of the present invention include, without limitation, avian, canine, equine, bovine, ovine, porcine, human or frog adenovirus. In a preferred embodiment the adenovirus of the invention is a human adenovirus, i.e. an adenovirus capable of infecting humans. According to the invention, a "serotype" is each of the immunologically different types of adenovirus. There are at least 57 serotypes of human adenovirus that are classified into several subgroups (A to G). The invention contemplates the use of any adenoviral serotype known in the state of the art including, without limitation, any of the serotypes defined in Table 1.

TABLE 1

Several examples of adenoviral subgroups and serotypes suitable for use in the present invention.

| Subgroup | Serotypes |
| --- | --- |
| A | 12, 18, 31 |
| B | 3, 7, 11, 14, 16, 21, 34, 35, 50, 55 |
| C | 1, 2, 5, 6, 57 |
| D | 8, 9, 10, 13, 15, 17, 19, 20, 22-30, 32, 33, 36-39, 42-49, 51, 53, 54, 56 |
| E | 4 |
| F | 40, 41 |
| G | 52 |

In a preferred embodiment, the human adenovirus is selected from the group consisting of human adenovirus serotypes 1 to 57.

In another preferred embodiment the adenovirus pertains to subgroup C, more preferably is serotype 5.

Human adenovirus serotype 5 (Ad5) is associated with mild respiratory infections. The gene sequence of human adenovirus serotype 5 can be found in GenBank: AY339865.1 (version of 13 Aug. 2007).

The adenovirus of the invention is a recombinant adenovirus. The term "recombinant", as used herein, refers to an adenovirus that does not appear naturally. This recombinant adenovirus contains one or more modifications with respect to the wild-type. Such modifications include, but are not limited to, modifications to the adenovirus genome that is packaged in the particle in order to make an infectious virus. Other modifications allow obtaining replication-deficient virus (i.e. virus that cannot reproduce) by removing a gene from the virus genome that is critical for replication. Exemplary modifications include deletions known in the art, such as deletions in one or more of the E1a, E1b, E2a, E2b, E3, or E4 coding regions. Other exemplary modifications include deletions of all of the coding regions of the adenoviral genome. Such adenoviruses are known as "gutless" adenoviruses. Chimeric adenoviruses formed by combination of elements from different serotypes are also included.

The term "recombinant" also includes replication-conditional adenoviruses, which are viruses that preferentially replicate in certain types of cells or tissues but to a lesser degree or not at all in other types. For example, among the adenoviruses provided herein, are adenoviruses that replicate in abnormally proliferating tissue, such as solid tumours and other neoplasms. These include the viruses disclosed in U.S. Pat. Nos. 5,998,205 and 5,801,029. Such viruses are sometimes referred to as "cytolytic" or "cytopathic" viruses (or vectors), and, if they have such an effect on neoplastic cells, are referred to as "oncolytic" viruses (or vectors).

In an embodiment the adenovirus is a replicative adenovirus, particularly an oncolytic adenovirus.

In another embodiment the adenovirus is a non-replicative adenovirus or a replication-deficient adenovirus. Replication-deficient adenovirus or non-replicating adenovirus are adenovirus unable to replicate in the target cell that are used in gene therapy as carriers of genes to target cells since the goal is to express the therapeutic gene within the cell and not the lysis of the cell.

The recombinant adenovirus of the present invention is modified by insertion of a heterologous sequence on the outer surface of the adenoviral hexon protein. Particularly, the heterologous sequence encodes for an albumin-binding moiety.

The adenovirus particle consists on a capsid that encloses the viral DNA. The term "capsid", as used herein, refers to the protein shell of a virus formed by subunits named capsomers that may be pentagonal or hexagonal. The adenoviral capsid has an icosahedral shape, which has 20 equilateral triangular faces. Most of the capsid is formed by the hexon protein and each vertex has a complex formed by penton base and fiber protein.

The term "adenoviral hexon protein" or "hexon protein" (formerly referred to as "protein II"), as used herein, refers to the major structural capsid protein found in adenoviruses that self-associates to form trimers, each in the shape of a hexagon. 240 hexon trimers are assembled to provide an adenoviral capsid. The hexon protein is essential for virus capsid assembly, determination of the icosahedral symmetry of the capsid and integrity of the capsid. The major structural features of the hexon protein are shared by adenoviruses across serotypes, but the hexon protein differs in size and immunological properties between serotypes. In the present invention, the term "hexon protein" encompasses the hexon protein of any adenovirus, including, without limitation, the protein defined by the sequence of the UniProt database with accession number P04133 dated 19 Feb. 2014 which corresponds to the hexon protein of human adenovirus C serotype 5; the protein defined by the sequence of the UniProt database with accession number P03277 dated 19 Feb. 2014 which corresponds to the hexon protein of human adenovirus C serotype 2; the protein defined by the sequence of the UniProt database with accession number P42671 dated 19 Feb. 2014 which corresponds to the hexon protein of avian adenovirus gall (strain Phelps); and the protein defined by the sequence of the UniProt database with accession number P11819 dated 19 Feb. 2014 which corresponds to the hexon protein of human adenovirus F serotype 40. The expression includes all the natural variants of hexon protein that appear naturally in other subgroups or serotypes.

In the present invention, the expression "outer surface of the hexon protein", refers to the regions of the hexon protein that are exposed on the surface of the capsid. In order to know if the albumin-binding moiety of the present invention has been introduced in the inner part or in the outer surface of the adenoviral hexon protein, an assay for detecting of binding to human serum albumin may be performed as disclosed in the experimental section of this patent application (for example, an ELISA assay) or an in vitro neutralization assay. If human serum albumin is capable of binding to the adenovirus, then the albumin-binding moiety has been introduced in the outer surface of the adenoviral hexon protein.

It has been reported that Loop 1 (L1) and Loop 2 (L2) of hexon protein are exposed on the outside of the viral capsomere structure. L1 contains six hypervariable regions (HVRs), i.e. HVR1 to HVR6 and L2 contains the seventh hypervariable region (HVR7).

The term "hypervariable region" or "HVR", as used herein, refers to a region varying in length and sequence between adenoviral serotypes forming part of surfaced exposed loops. There are seven hypervariable regions of the adenoviral hexon for each subunit of the trimer (Biere B and Schweiger B. J Clin Virol 2010; 47(4):366-371). In the context of the present invention, the nomenclature used for the HVRs is as disclosed in Crawford-Miksza and Schnurr (Crawford-Miksza and Schnurr. 1996. Virology, 224(2):357-367). In a preferred embodiment of the present invention, the HVR is HVR1. Insertion of a specific residue in the HVR region results in 240 times×3 or 720 total inserts per adenoviral vector. In a preferred embodiment the sequence encoding the albumin-binding moiety is inserted so that the resulting fusion protein contains the albumin-binding moiety after the D150 amino acid of the hexon protein according to the numbering of the hexon protein having the GenBank accession number BAG48782.1 dated 14 Jun. 2008 corresponding to hexon protein from human adenovirus serotype 5 (SEQ ID NO: 27). In a more preferred embodiment, the nucleotide sequence of the complete modified adenoviral hexon having ABD inserted in HVR1 (ABD-HVR1) is SEQ ID NO: 3. The inventors have demonstrated that insertion of the albumin-binding domain in another HVR (specifically HVR5) produces viable virus but does not protect adenovirus from neutralizing antibodies. Examples of the present patent application show that the sequence encoding the albumin-binding moiety is inserted in HVR5 so that the resulting fusion protein contains the albumin-binding moiety after the A274 amino acid of the hexon protein according to the numbering of the hexon protein having the GenBank accession number BAG48782.1 dated 14 Jun. 2008 corresponding to hexon protein from human adenovirus serotype 5 (SEQ ID NO: 27). The nucleotide sequence of the complete modified adenoviral hexon having ABD inserted in HVR5 (ABD-HVR5) is SEQ ID NO: 4. FIG. 12 shows that the albumin-binding domain is functional when inserted in HVR1 but not in HVR5.

The albumin-binding moiety may be directly attached to the hexon protein, i.e. the N- and C-terminus of the albumin-binding moiety are linked directly to the hexon protein. However, it is also possible that the albumin-binding moiety is connected to the hexon protein by means of a linker sequence. Thus, in another embodiment, the N- and/or the C-terminus of the albumin-binding moiety is connected to the hexon protein by a linker sequence.

The term "linker sequence", as used herein, refers to an amino acid sequence that acts as a hinge region between the hexon protein and the albumin-binding moiety, providing space between both elements and assuring that the secondary structure of hexon protein is not affected by the presence of the ABD moiety and vice versa. The linker sequence may be of any length that allows both elements to move independently from one another while maintaining the three-dimensional form of the individual elements. In a preferred embodiment, the linker sequence is a flexible linker peptide with a length of 31 amino acids or less. More preferably, the linker sequence comprises less than 10 amino acids, less than 5 amino acids, less than 4 amino acids or 2 amino acids. In an embodiment, the linker sequence comprises 2 or more amino acids selected from the group consisting of glycine, serine, alanine and threonine. In another embodiment, said linker is a polyglycine linker. Exemplary, non-limitative, examples of linker sequences include SGGTSGSTSGTGST (SEQ ID NO: 5), AGSSTGSSTGPGSTT (SEQ ID NO: 6), GGSGGAP (SEQ ID NO: 7) and GGGVEGGG (SEQ ID NO: 8). These sequences have been used for binding designed coiled coils to other protein domains (Muller, K. M. et al. Meth. Enzymology, 2000, 328:261-281). Preferably, the linker sequence comprises the sequence GSGS (SEQ ID NO: 2). Other linkers known in the art could be used alternatively (Reddy Chichili, V P., Kumar, V., and Sivaraman, J. (2013). Linkers in the structural biology of protein-protein interactions. Protein Science 22(2):153-67).

Therefore, the adenovirus of the present invention has an albumin-binding moiety on the outer surface of the hexon protein, thus coating the capsid of the adenovirus with albumin.

The term "albumin", as used herein, refers to a member of the albumin family proteins that are water-soluble globular proteins, moderately soluble in concentrated salt solutions and experiencing heat denaturation. Albumins are commonly found in blood plasma. Serum albumin is produced by the liver, is dissolved in blood plasma and is the most abundant blood protein in mammals. Particularly, the term "serum albumin" refers to a globular protein that in humans is encoded by the ALB gene (UniGene Hs. 418167). Human serum albumin protein is the protein defined by the sequence of the Uniprot database with accession number P02768 dated 19 Mar. 2014.

The term "albumin-binding moiety", as used herein, refers to any amino acid sequence capable of binding to albumin, i.e. having albumin binding affinity. Preferably, it is capable of binding serum albumin, more preferably human serum albumin. The term "albumin-binding moiety" includes, without limitation, naturally-occurring albumin-binding domains (ABD) (such as ABD present in bacterial proteins), and albumin-binding sequences from synthetic peptides. In a preferred embodiment, the albumin-binding moiety is selected from an albumin-binding domain from streptococcal protein G, an albumin-binding domain from *Peptostreptococcus magnus* protein PAB, an albumin-binding peptide having the core sequence DICLPRWGCLW (SEQ ID NO: 9) and functionally equivalent variants thereof. In a more preferred embodiment, the albumin-binding domain is from streptococcal protein G.

The term "albumin binding domain" refers to any region from a naturally occurring protein which is capable of binding albumin with sufficient specificity so as to ensure protection from neutralizing antibodies.

The term "albumin-binding domain from streptococcal protein G", or "ABD from streptococcal protein G", as used herein, refers to a domain that consists of 46 amino acid residues forming a three-helix bundle (Kraulis P. J. et al. FEBS Lett, 1996; 378:190-4), and binds with high affinity to both human and mouse albumin, but not to bovine albumin (Konig T. and Skerra A. J Immunol Methods, 1998; 218: 73-83). There are multiple albumin-binding domains in streptococcal protein G. In a preferred domain the albumin-binding moiety is the albumin-binding domain 3 from streptococcal protein G. Preferably, the sequence of the albumin-binding domain 3 from streptococcal protein G is SEQ ID NO: 1.

The term "albumin-binding domain from *Peptostreptococcus magnus* protein PAB", as used herein, refers to the albumin-binding domain from protein PAB of *Finegoldia magna* (formerly known as *Peptostreptococcus magnus*) known as the "GA module" that is capable of binding albumin (Lejon S et al. 2004. J Biol Chem 279:42924-42928). Protein PAB of *Finegoldia magna* is the protein defined by the sequence of the GenBank database with accession number CAA54857.1 dated 9 Sep. 2004.

The term "albumin-binding peptide having the core sequence DICLPRWGCLW (SEQ ID NO: 9)", as used herein, refers to peptides that bind albumin derived from phage clones RA and SA as disclosed in Dennis M S et al. (J Biol Chem. 2002. 277:35035-35043).

The invention also encompasses functionally equivalent variants of such albumin-binding moieties. The term "functionally equivalent variant", as used herein, refers to any polypeptide derived from an albumin-binding moiety by insertion, deletion or substitution of one or more residues and which maintains substantially the ability to interact with the albumin as determined above. In a preferred embodiment, a polypeptide is considered a functionally equivalent variant of an albumin-binding moiety if it shows an ability in binding to albumin that is at least 10%, 20%, 30%, 40%, 50%, 60%, 70%, 80%, 90% or 100% of the ability in binding to albumin of the albumin-binding domain of SEQ ID NO: 1. Preferably, a polypeptide is considered a functionally equivalent variant of an albumin-binding moiety if it is capable of neutralizing antibodies at least 10%, 20%, 30%, 40%, 50%, 60%, 70%, 80%, 90% or 100% as efficiently as the albumin-binding domain of SEQ ID NO: 1.

Suitable functional variants are those showing a degree of identity with respect to the albumin-binding domains or albumin-binding sequences disclosed in the present invention of at least 25% amino acid sequence identity, such as at least 30%, at least 40%, at least 50%, at least 60%, at least 70%, at least 80%, at least 90%, at least 91%, at least 92%, at least 93%, at least 94%, at least 95%, at least 96%, at least 97%, at least 98% or at least 99%. The degree of identity between two polypeptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)], though other similar algorithms can also be used. BLAST and BLAST 2.0 are used, with the parameters described herein, to determine percent sequence identity. Software for performing BLAST analyses is publicly available through the National Center for Biotechnology Information.

The functionally equivalent variants of the albumin-binding moieties can be derivatives of the albumin-binding domains and albumin-binding sequences. The term "derivatives" includes, without limitation, albumin-binding domains from bacteria modified to increase their affinity to albumin, as those disclosed in Johansson M U. et al. (J Biol Chem. 2002. 277:8114-8120), Jonsson A. et al. (Protein Eng Des Sel. 2008. 21: 515-527) and Linhult M. et al. (Protein Sci. 2002. 11:206-213). For example, a derivative may be the modified streptococcal G ABD ABD035 disclosed in Jonsson A. et al. (Protein Eng Des Sel. 2008. 21: 515-527).

Recombinant adenoviruses may be obtained by standard molecular biology techniques known in the state of the art (Chillon and Bosch. Adenovirus. Methods and Protocols. 3rd edition. Methods in Molecular Biology, vol. 1089. Springer Protocols. Humana Press. (2014)).

The adenovirus that contains the albumin-binding moiety of the present invention is propagated and amplified following the standard methods in the field of adenoviral vectors as disclosed in Chillon and Bosch. Adenovirus. Methods and Protocols. 3rd edition. Methods in Molecular Biology, vol. 1089. Springer Protocols. Humana Press. (2014); and Alemany R, Zhang W. Oncolytic adenoviral vectors. Totowa, N.J.: Humana Press, 1999. Cell lines normally used in the field of gene therapy and virotherapy are HEK-293 and A549 cell lines. The preferred method for propagation is by infection of a cell line that allows the replication of adenovirus. The lung adenocarcinoma A549 cell line is an example of such a cell line. The propagation is carried out, for example, as follows: A549 cells are seeded on plastic cell culture plates and infected with 100 viral particles per cell. Two days later the cytopathic effect evidences the viral production when cells detach forming "grape-like" clusters. The cells are harvested in tubes. After centrifugation at 1000 g during 5 minutes, the cell pellet is frozen and thawed three times to break the cells. The resulting cell extract is centrifuged at 1000 g during 5 minutes and the supernatant containing the virus is layered onto a cesium chloride gradient and centrifuged during 1 hour at 35000 g. The band of virus obtained from the gradient is collected and layered again onto another gradient of cesium chloride and centrifuged during 16 hours at 35000 g. The virus band is collected and dialyzed against PBS-10% glycerol. The dialyzed virus is aliquoted and kept at −80° C. The quantification of the number of viral particles and plaque-forming units is done following standard protocols. Phosphate buffered saline (PBS) with 5% glycerol is a standard formulation used for the storage of adenovirus. Nevertheless other formulations that improve the stability of the virus have been described.

The methods of purification of the adenoviruses that contain the albumin-binding moiety for its use in the prevention or treatment of cancer are the same as those described for other adenoviruses and adenoviral vectors used in virotherapy and gene therapy of cancer.

Adenovirus can be used to target abnormal cells, for example, any cells which are harmful or otherwise unwanted in vivo. Broad examples include cells causing autoimmune disease, restenosis, and scar tissue formation.

The adenoviruses of the invention can be selectively distributed in vivo in a given tissue, avoiding or significantly reducing expression in non-target or non-tumour tissue.

The replicative adenovirus of the invention may have modifications in its genomic sequence that confer selective replication in a cell. In order to direct the expression of the adenovirus to the tissue wherein such expression is needed or to the tumoural tissue to be treated, the adenovirus of the invention may comprise a tissue-specific promoter or a tumour-specific promoter. Thus, in an embodiment, the adenovirus further comprises a tissue-specific promoter or a tumour-specific promoter.

In a preferred embodiment, the tissue-specific promoter or the tumour-specific promoter are promoter sequences to control the expression of one or more genes selected from the group consisting of E1a, E1b, E2, and E4. Preferably, the promoter controls the expression of E1a.

The term "promoter", as used herein, is used according to its art-recognized meaning. It is intended to mean the DNA region, usually upstream to the coding sequence of a gene, which binds RNA polymerase and directs the enzyme to the correct transcriptional start site. Said promoter controls the viral genes that start the replication.

The term "tissue-specific" is intended to mean that the promoter to which the gene essential for replication is operably linked functions specifically in that tissue so that replication proceeds in that tissue. This can occur by the presence in that tissue, and not in non-target tissues, of positive transcription factors that activate the promoter. It can also occur by the absence of transcription inhibiting factors that normally occur in non-target tissues and prevent transcription as a result of the promoter. Thus, when transcription occurs, it proceeds into the gene essential for replication such that in a target tissue, replication of the vector and its attendant functions occur.

Tissue specificity is particularly relevant with respect to targeting an abnormal counterpart of a particular tissue type while avoiding the normal counterpart of the tissue, or avoiding surrounding tissue of a different type than the abnormal tissue, while treating the abnormal tissue. In a particular embodiment, the promoter is "tumour-specific", which means that the promoter functions specifically in tumoural tissues. For example, the recombinant adenoviruses of the invention are useful for treating metastases to the liver. One specific example is colon cancer, which often metastasizes into the liver. It has been found that even when colon cancer metastasizes into the liver, the CEA promoter is active in the cells of the metastases but not in normal liver cells. Accordingly, normal human adult liver should not support replication of a virus that has viral genes essential for replication linked to the colon cancer CEA-specific promoter. Replication should occur in the primary cancer cells. Another example is the alphafetoprotein promoter, which is active only in hepatocellular carcinoma. A further example is the tyrosinase promoter, which is active only in melanoma and not in normal skin. In each case, replication is expected in the abnormal but not the normal cells.

Examples of tissue-specific promoters are, without limitation, alphafetoprotein promoter, DE3 promoter, tyrosinase promoter, carcinoembryonic antigen (CEA) promoter, surfactant protein promoter, E2F promoter, telomerase hTERT promoter, prostate-specific antigen promoter, COX-2 promoter, albumin gene promoter, the core promoter of hepatitis virus, the promoter of the globulin-binding protein which binds to thyroxine and ErbB2 promoter.

In a preferred embodiment, the promoter is selected from the group consisting of a E2F promoter, a telomerase hTERT promoter, a tyrosinase promoter, a prostate-specific antigen promoter, an alphafetoprotein promoter, and a COX-2 promoter.

The adenoviruses of the invention are particularly useful for the treatment of cancer. All tumours are potentially amenable to treatment with the adenovirus of the invention. Tumour types include, but are not limited to, hematopoietic, pancreatic, neurologic, hepatic, gastrointestinal tract, endocrine, biliary tract, sinopulmonary, head and neck, soft tissue sarcoma and carcinoma, dermatologic, reproductive tract, and the like. Preferred tumours for treatment are those with a high mitotic index relative to normal tissue, preferably solid tumours.

In a preferred embodiment, the adenovirus of the invention is an oncolytic adenovirus.

The term "oncolytic adenovirus", as used herein, refers to any adenovirus that is able to replicate or that is replication-competent in the tumour cell, even without selectivity. The therapeutic action of oncolytic adenoviruses is based on the capability to replicate and to lyse the tumour cell to be eliminated. The death of the tumour cells can be detected by any method of the state of the art, such as determining the number of viable cells, the cytopathic effect, the apoptosis of tumour cells, the synthesis of viral proteins in tumour cells (for example, by metabolic labelling, Western blot of viral proteins or PCR with reverse transcription of the viral genes needed for replication) or the reduction in the size of the tumour.

Another strategy to achieve selective replication in tumours is the deletion of viral functions that are necessary for replication in normal cells but that are not needed in tumour cells. This includes, for example, the deletion of early E1A functions which block the retinoblastoma (pRB) pathway. The selective replication of such mutants has been demonstrated in several prior art documents. Other viral genes that interact directly with pRB such as E4 and E4orf6/7 are candidates to be deleted in order to achieve selective replication in tumour cells.

Another modification described to achieve selective replication in tumours is the deletion of adenoviral genes coding for the virus-associated RNAs (VA-RNAs). These RNAs block the antiviral activity of interferon and their deletion results in adenoviruses that are sensitive to interferon inhibition. Due to the characteristic truncation in the interferon pathway in tumour cells such adenoviruses replicate normally in tumours.

Therefore, in another embodiment the adenovirus of the invention further comprises mutations in one or more genes selected from the group consisting of E1a, E1b, E4, and VA-RNAs, to achieve selective replication in tumours. Preferably the mutations are in E1a. In a preferred embodiment the mutation in E1a is a deletion of some amino acids of the E1A protein affecting the interaction of E1A with pRB, preferably is a deletion of the amino acids 121-129 of the polypeptide chain (Δ24 deletion).

The expression "selective replication", as used herein, means that the adenovirus has replication efficiency in tumour cells higher than in normal cells (for example 1000-fold higher than in normal cells).

The term "replication", as used herein, refers to the duplication of adenoviral vectors that occur at the level of nucleic acid or at the level of infectious viral particle. In the case of DNA viruses, replication at the nucleic acid level is DNA replication. However, replication also includes the formation of infectious DNA viral particles.

Replication of an adenovirus can be assayed by well-known techniques. Assays for replication of an adenoviral vector in a cell generally involve detecting a polynucleotide, virions or infective virus. A variety of well-known methods that can be used for this purpose involve determining the amount of a labelled substrate incorporated into a polynucleotide during a given period in a cell.

When replication involves a DNA polynucleotide, $^3$H-thymidine often is used as the labelled substrate. In this case, the amount of replication is determined by separating DNA of the vector from the bulk of cellular DNA and measuring the amount of tritium incorporated specifically into vector DNA.

Replication of a polynucleotide vector also may be detected by lysing or permeating cells to release the polynucleotide, then isolating the polynucleotide and quantitating directly the DNA or RNA that is recovered. Polynucleotide replication also may be detected by quantitative PCR using primers that are specific for the assayed polynucleotide.

Virions may be assayed by electron microscope counting techniques well known to the art, by isolating the virions and determining protein and nucleic acid content, and by labelling viral genomic polynucleotides or virion proteins and determining the amount of virion from the amount of polynucleotide or protein.

Another strategy to achieve selectivity of an adenovirus towards a tumour cell is the modification of the virus capsid proteins implied in the infection of the host cell to target the adenovirus to a receptor present in a tumour cell. The modification of the capsid proteins that the virus uses to infect the cells may also be used to increase infectivity of the adenovirus (i.e. increasing the entry of the virus in the cell). Targeting adenovirus to the tumour can also be achieved with bifunctional ligands that bind to the virus in one end and to the tumour receptor in the other.

Thus, in another embodiment the adenovirus of the invention further comprises capsid modifications to increase its infectivity or to target it to a receptor present in a tumour cell. In a more preferred embodiment, the modification of the capsid is the insertion of an RGD motif (Arginine-Glycine-Asparagine motif) into the H1 loop of the adenoviral fiber protein. This insertion allows the adenovirus to use integrins to dock in the cell and not only to internalize as it is the case with wild-type adenovirus. The use of integrins as cellular receptors of the virus increases the infectivity and the oncolytic potency. In another embodiment, the oncolytic adenovirus has the capsid modified by means of a replacement of the KKTK (SEQ ID NO: 10) heparan sulphate binding domain in the adenovirus fibre with the domain RGDK (SEQ ID NO: 11) (N. Bayo et al. Human Gene Therapy 2009, 20:1214-21). Another strategy to increase infectivity of target cells with adenoviruses is the replacement of a portion of the fiber with the homologous portion from a different serotype. Commonly the fiber shaft and knob of human adenoviruses derived from serotype 5 have been replaced with the fiber shaft and knob of human serotype 3 or 35 adenoviruses. The obtained recombinant adenoviruses with genomes derived from different serotypes are known in the art as chimeric adenoviruses. In another embodiment the adenovirus of the invention further comprises a chimeric capsid derived from different adenovirus serotypes. In another preferred embodiment, the modification of the capsid is the substitution of part of the fiber gene with the homologous part from a different adenovirus serotype to form a chimeric adenovirus.

In a preferred embodiment, the oncolytic adenovirus is a tumour-selective replicating adenovirus characterized by containing a mutant version of the E1A protein where amino acids 121-129 of the polypeptide chain have been deleted (Δ24 deletion) affecting the interaction of E1a with pRB, the insertion of four E2F binding sites and one Sp1 binding site in the endogenous promoter of E1a to control the expression of E1a, and finally, the insertion of the RGD peptide in the adenoviral fibre to increase the infectivity of the virus. ICOVIR15-ABD is a preferred embodiment of the invention. Said modifications may be present in combination in the same adenovirus or in isolation.

In a preferred embodiment, the oncolytic adenovirus is a tumour-selective replicating adenovirus characterized by containing a deletion of some amino acids of the E1A protein affecting the interaction of E1A with pRB, preferably a deletion of the amino acids 121-129 of the polypeptide chain (Δ24 deletion).

In another preferred embodiment, the oncolytic adenovirus is a tumour-selective replicating adenovirus characterized by containing an insertion of four E2F binding sites and one Sp1 binding site in the endogenous promoter of E1a to control the expression of E1a.

In another preferred embodiment, the oncolytic adenovirus is a tumour-selective replicating adenovirus characterized by containing the insertion of the RGD peptide in the adenoviral fibre to increase the infectivity of the virus.

The genome of the adenovirus can also contain a heterologous gene that encodes a therapeutic protein such that the heterologous gene is expressed within an infected cell. A therapeutic protein, as used herein, refers to a protein that would be expected to provide some therapeutic benefit when expressed in a given cell. Said heterologous gene products may be contained in replicating or non-replicating adenovirus. The therapeutic gene inserted may be any gene used in gene therapy or in vaccination. Preferably, the heterologous gene is used in cancer gene therapy. The insertion of a therapeutic gene in the genome of the oncolytic adenovirus generates an "armed oncolytic adenovirus" that increase the cytotoxicity of oncolytic adenovirus towards tumour cells. For example, said heterologous gene can produce the death of the tumour cell, activate the immune system against the tumour, inhibit the angiogenesis, eliminate the extracellular matrix, induction of the apoptosis, among others. In these cases, the way and the time of expression of the therapeutic gene will be critical in the final result of the therapeutic approach.

Therefore, in an embodiment, the adenovirus comprises one or more non-adenoviral genes inserted in the genome of said adenovirus. In a preferred embodiment, the genes are genes used in gene therapy or in vaccination. In a more preferred embodiment the genes are genes used in cancer gene therapy. Preferably, the genes used in cancer gene therapy are at least a gene selected from the group consisting of prodrug-activating genes, tumour-suppressor genes, genes encoding anti-tumour interfering RNAs and immunostimulatory genes.

The term "non-adenoviral gene", as used herein, refers to a heterologous gene not present in the genome of a wild-type adenovirus.

The term "gene used in gene therapy", as used herein, refers to a gene that can be used as a drug to prevent or treat a genetic or acquired disease or condition by delivering said therapeutic DNA into patient's cells. As the person skilled in the art understands, the term gene therapy involves using DNA that encodes a functional, therapeutic gene to replace a mutated gene or using DNA that encodes a therapeutic protein. For example, the DNA can encode an enzyme, hormone, receptor or polypeptide of therapeutic value. Any gene that can be used to treat a disease that is suitable treated by gene therapy may be inserted in the adenoviral genome of the adenovirus of the invention. Genes used in gene therapy can be, without limitation, genes coding for enzymes, blood derivatives, hormones, interleukins, interferons, TNF, growth factors, neurotransmitters or their precursors or synthetic enzymes, trophic factors, namely BDNF, CNTF, NGF, IGF, GMF, aFGF, bFGF, NT3, NT5 and the like; apolipoproteins, namely ApoAI, ApoAIV, ApoE, and the like; dystrophin or a minidystrophin;

tumour-suppressor genes, namely p53, Rb, RapIA, DCC, k-rev; genes coding for factors involved in coagulation, namely factors VII, VIII, IX; prodrug-activating genes, namely thymidine kinase, cytosine deaminase; all or part of a natural or artificial immunoglobulin (Fab, ScFv, and the like). The therapeutic gene can also be an antisense gene or sequence whose expression in the target cell enables gene expression or transcription of cellular mRNAs to be controlled.

The term "gene used in vaccination", as used herein, refers to a gene coding for an antigenic peptide, capable of generating an immune response in man or animals for the purpose of preventive or therapeutic vaccine production. Such antigenic peptides may be, without limitation, those specific to the Epstein-Barr virus, the HIV virus, the hepatitis B virus, the pseudorabies virus and tumour-specific peptides.

The term "prodrug-activating genes", as used herein, refers to genes encoding a product that acts on a non-toxic prodrug, converting the non-toxic prodrug into a form that is toxic for the target tissue. Preferably, the toxin has anti-tumour activity or eliminates cell proliferation.

Examples of prodrug-activating genes include, without limitation, thymidine kinase gene. Herpes simplex virus thymidine kinase phosphorylates ganciclovir to produce the nucleotide toxin ganciclovir phosphate. This compound functions as a chain terminator and DNA polymerase inhibitor, prevents DNA synthesis and thus is cytotoxic. In an embodiment the prodrug-activating gene is thymidine kinase gene, preferably a viral thymidine kinase selected from the group consisting of Herpes simplex virus thymidine kinase, cytomegalovirus thymidine kinase and varicella-zoster virus thymidine kinase. When viral thymidine kinases are employed, the interaction or chemotherapeutic agent preferably is a nucleoside analogue, for example, one selected from the group consisting of ganciclovir, acyclovir, and 1-2-deoxy-2-fluoro-D-arabinofuranosil-5-iodouracil (FIAU). Such interaction agents are utilized efficiently by the viral thymidine kinases as substrates, and such interaction agents thus are incorporated lethally into the DNA of the tumour cells expressing the viral thymidine kinases, thereby resulting in the death of the target cells. In another embodiment the prodrug-activating gene is cytosine deaminase. Cytosine deaminase converts 5'-fluorocytosine to the anti-cancer drug 5'-fluorouracil, which is highly cytotoxic. Thus, the target cell which expresses the cytosine deaminase gene converts the 5-fluorocytosine to 5-fluorouracil and are killed. For a discussion of such "suicide" genes, see Blaese, R. M. et al., *Eur. J. Cancer* 30A:1190-1193 (1994).

The term "tumour-suppressor genes", as used herein, refers to anti-oncogenes or genes that protect a cell from one step on the path to cancer. When one of these genes mutates to cause a loss or reduction in its function, the cell can progress to cancer, usually in combination with other genetic changes.

Examples of tumour-suppressor genes are, without limitation, p53 tumour-suppressor protein encoded by the TP53 gene, PTEN, pVHL, APC, CD95, ST5, YPEL3, ST7, and ST14.

The term "genes encoding antitumour interfering RNAs", as used herein, refers to genes that encode therapeutically useful RNA molecules for the treatment of tumours, i.e. siRNA (Dorsett and Tuschl (2004) Nature Rev Drug Disc 3:318-329). In some cases, genes can be incorporated into a recombinant adenovirus of the invention to further enhance the ability of the adenovirus to eradicate the cell of the monocyte/macrophage lineage, although not having any direct impact on the cell itself. These include genes encoding siRNAs capable of inhibit the activity of factors that compromise MHC class I presentation, block complement, inhibit IFNs and IFN-induced mechanisms, chemokines and cytokines, NK cell based killing, down regulate the immune response (e.g. IL-10, TGF-Beta) and metalloproteases which can breakdown the extracellular matrix and enhance spread of the virus within the tumour.

The term "immunostimulatory genes", as used herein, refers to genes that activate the immune system against the tumour. Further examples of heterologous genes, or fragments thereof, include those that encode immunomodulatory proteins, such as cytokines or chemokines. Examples include interleukin 2, U.S. Pat. No. 4,738,927 or 5,641,665; interleukin 7, U.S. Pat. No. 4,965,195 or 5,328,988; and interleukin 12, U.S. Pat. No. 5,457,038; tumour necrosis factor alpha, U.S. Pat. No. 4,677,063 or 5,773,582; interferon gamma, U.S. Pat. No. 4,727,138 or 4,762,791; or GM CSF, U.S. Pat. No. 5,393,870 or 5,391,485, Mackensen et al. (1997) Cytokine Growth Factor Rev. 8:119-128).

These modifications in the genome of the adenovirus are not excluding each other.

Adenoviral Genomes of the Invention

The present invention is also directed to the genome of the adenovirus. In an aspect, the invention relates to an adenoviral genome characterized in that it comprises a sequence encoding an albumin-binding moiety inserted in the coding region of the hypervariable region 1 (HVR1) of the hexon protein which results in the expression of fusion protein comprising a hexon protein and an albumin-binding moiety and wherein the albumin-binding moiety is located on the outer surface of the hexon protein when the hexon protein is assembled in the adenovirus capsid.

The expression "adenoviral genome", as used herein, refers to a double-stranded DNA sequence that, in the presence of appropriate proteins, can be packaged, resulting in a complete adenovirus particle. For this packaging to occur, the sequence must comply with some conditions, which can be summarized as follows:

- exhibit separate adenovirus ITR, one at each of its end points;
- comprise a packaging signal Psi between both ITRs, located in such a way that the distance between the 5' end of the packaging signal Psi and the 3' end of the ITR closest to it does not exceed the distance that would prevent packaging of the natural adenovirus, a distance that is 200 base pairs in the case of the human serotype 5 adenovirus and which is assumed, by analogy, to be approximately equal in the case of other serotypes, since it has been seen that the introduction of sequences between the ITR and the packaging signal in the sequence that naturally separates them decreases the packaging capacity of the adenoviral genome, causing a reduction in the total number of adenovirus particles obtained, even though there is no significant change in the time necessary for their packaging;
- the distance between the ends of both ITR should not be greater than 105 percent of the size of the adenovirus genome present in nature to which the proteins which will form the capsid belong.

The adenoviral genome is preferably deficient in at least one gene function required for viral replication, thereby resulting in a "replication-deficient" adenoviral vector. By "replication-deficient" is meant that the adenoviral vector comprises an adenoviral genome that lacks at least one replication-essential gene function (i.e., such that the adenoviral vector does not replicate in typical host cells, especially those in a human patient that could be infected by the adenoviral vector in the course of treatment in accordance with the invention).

More preferably, the replication-deficient adenoviral vector comprises an adenoviral genome deficient in at least one replication-essential gene function of one or more regions of the adenoviral genome. In this respect, the adenoviral vector is deficient in at least one essential gene function of the E4 region or E1 region of the adenoviral genome required for viral replication. In addition to a deficiency in the E1 region, the recombinant adenovirus can also have a mutation in the major late promoter (MLP). More preferably, the adenoviral vector is deficient in at least one essential gene function of the E1 region and at least part of the E3 region (e.g., an Xba I deletion of the E3 region). With respect to the E1 region, the adenoviral vector can be deficient in (e.g., deleted of) at least part of the E1a region and at least part of the E1b region. For example, the adenoviral vector can comprise a deletion of the entire E1 region and part of the E3 region of the adenoviral genome (i.e., nucleotides 355 to 3,511 and 28,593 to 30,470). A singly-deficient adenoviral vector can be deleted of approximately nucleotides 356 to 3,329 and 28,594 to 30,469 (based on the adenovirus serotype 5 genome). Alternatively, the adenoviral vector genome can be deleted of approximately nucleotides 356 to 3,510 and 28,593 to 30,470 (based on the adenovirus serotype 5 genome), thereby resulting in an adenoviral vector having deletions in the E1, E3, and E4 regions of the adenoviral genome.

A deficiency in a gene, gene function, or gene or genomic region, as used herein, is defined as a deletion of sufficient genetic material of the viral genome to impair or obliterate the function of the gene whose nucleic acid sequence was deleted in whole or in part. Deletion of an entire gene region often is not required for disruption of a replication-essential gene function. However, for the purpose of providing sufficient space in the adenoviral genome for one or more transgenes, removal of a majority of a gene region may be desirable. While deletion of genetic material is preferred, mutation of genetic material by addition or substitution also is appropriate for disrupting gene function. Replication-essential gene functions are those gene functions that are required for replication (e.g., propagation) and are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., NA-RNA-1 and/or NA-RNA-2).

The adenoviral vector also can have essentially the entire adenoviral genome removed except the ITR and the packaging sequence. Such vectors are known in the art as gutless or helper-dependent adenovirus vectors. In this case the hexon sequence modified to contain an albumin binding moiety is provided by the helper adenovirus. The 5' or 3' regions of the adenoviral genome comprising ITRs and packaging sequence need not originate from the same adenoviral serotype as the remainder of the viral genome. For example, the 5' region of an adenoviral serotype 5 genome (i.e., the region of the genome 5' to the adenoviral E1 region) can be replaced with the corresponding region of an adenoviral serotype 2 genome (e.g., the Ad5 genome region 5' to the E1 region of the adenoviral genome is replaced with nucleotides 1-456 of the Ad2 genome). However, the deficiencies of the adenoviral genome of the adenoviral vector of the inventive method preferably are limited to replication-essential gene functions encoded by the early regions of the adenoviral genome.

According to the invention, inverted terminal repeat or ITR is understood as sequences of approximately 100 base pairs which are on both sides of the linear genome of the adenovirus and which are essential for the replication of the adenoviral genome (Stow, N. D., 1982, Nucl. Acid. Res, 10:5105-5109).

According to the invention, adenoviral packaging signal ψ is understood as a sequence of approximately 160 base pairs long which, in the case of the adenovirus of serotypes 2 and 5, extends between positions 190 and 350 of the genome. The elimination of the sequence of the genome of an adenovirus prevents the DNA molecules which are generated during the multiplication of the virus from being efficiently incorporated to the recently formed capsids (Hearing, P. et al., 1987, J. Virol., 61:2555-2558), but they do not prevent the replication of said genome in the packaging cell, unlike the elimination of ITRs.

All the embodiments disclosed in the context of the adenoviruses of the invention are applicable to the adenoviral genomes of the invention.

Particularly, in an embodiment the adenoviral genome is from a human adenovirus, preferably selected from the group consisting of human adenovirus serotypes 1 to 57, more preferably serotype 5.

In another embodiment the albumin-binding moiety is selected from an albumin-binding domain from streptococcal protein G, an albumin-binding domain from *Peptostreptococcus magnus* protein PAB, an albumin-binding peptide having the core sequence DICLPRWGCLW (SEQ ID NO: 9) and functionally equivalent variants thereof. In a more preferred embodiment, the albumin-binding moiety is the albumin-binding domain 3 from streptococcal protein G, preferably having the sequence SEQ ID NO: 1.

In another embodiment the sequence encoding the albumin-binding moiety is inserted so that the resulting fusion protein contains the albumin-binding moiety after the D150 amino acid of the hexon protein according to the numbering of the hexon protein having the GenBank accession number BAG48782.1 (SEQ ID NO: 27). In a preferred embodiment, the nucleotide sequence of the complete modified adenoviral hexon having ABD inserted in HVR1 (ABD-HVR1) is SEQ ID NO: 3.

In another embodiment the N- and/or the C-terminus of the albumin-binding moiety is connected to the hexon protein by a linker sequence, preferably a linker sequence comprising the sequence GSGS (SEQ ID NO: 2).

In another embodiment the adenoviral genome further comprises a tissue-specific promoter or a tumour-specific promoter. In a preferred embodiment the tissue-specific promoter or the tumour-specific promoter are promoter sequences to control the expression of one or more genes selected from the group consisting of E1a, E1b, E2, and E4; more preferably a promoter selected from the group consisting of a E2F promoter, a telomerase hTERT promoter, a tyrosinase promoter, a prostate-specific antigen promoter, an alpha-fetoprotein promoter, and a COX-2 promoter.

In another embodiment the adenovirus is an oncolytic adenovirus, preferably an adenovirus wherein its adenoviral genome further comprises mutations in one or more genes selected from the group consisting of E1a, E1b, E4, and VA-RNAs, to achieve selective replication in tumours.

In another embodiment the adenoviral genome further comprises capsid modifications to increase adenovirus infectivity or to target it to a receptor present in a tumour cell. Preferably, the modification of the capsid is the insertion of an RGD motif into the H1 loop of the adenoviral fiber protein. In another embodiment the adenoviral genome is a chimeric adenovirus genome derived from one given serotype that contains a fragment or portion of its genome replaced by the homologous portion of the genome from another serotype. Preferably, the said chimeric adenovirus is a human adenovirus from the serotype 5 which contains a portion of the fiber gene replaced with the homologous portion from another serotype, preferably human adenovirus 3 or human adenovirus 35. In a preferred embodiment, the modification of the capsid is the substitution of part of the fiber gene with the homologous part from a different adenovirus serotype to form a chimeric adenovirus.

In another embodiment, the adenoviral genome comprises further genes inserted in said genome. In an embodiment, said genes are used in gene therapy or in vaccination. Preferably, said genes are genes used in cancer gene therapy, more preferably are at least a gene selected from the group consisting of prodrug-activating genes, tumour-suppressor genes, genes encoding anti-tumour interfering RNAs, and immunostimulatory genes.

Compositions of the Invention

The recombinant adenoviruses of the invention can be used to prepare a pharmaceutical composition. Thus, another aspect of the present invention is a pharmaceutical composition comprising a therapeutically effective amount of a recombinant adenovirus according to the invention together with a pharmaceutically acceptable carrier.

As it is used in the present invention, the expression "pharmaceutical composition" relates to a formulation that has been adapted for administering a predetermined dose of one or several therapeutic useful agents to a cell, a group of cells, an organ, a tissue or an organism.

The recombinant adenoviruses are administered in effective amounts. A "therapeutically effective amount" is understood as an amount capable of providing a therapeutic effect, and which can be determined by the person skilled in the art by commonly used means. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. It is preferred generally that a maximum dose be used, that is, the highest safe dose according to sound medical judgment. For example, if the subject has a tumour, an effective amount may be that amount that reduces the tumour volume or load (as for example determined by imaging the tumour). Effective amounts may also be assessed by the presence and/or frequency of cancer cells in the blood or other body fluid or tissue (e.g., a biopsy). If the tumour is impacting the normal functioning of a tissue or organ, then the effective amount may be assessed by measuring the normal functioning of the tissue or organ. Those skilled in the art will appreciate that dosages may also be determined with guidance from Goodman and Goldman's The Pharmacological Basis of Therapeutics, Ninth Edition (1996), Appendix II, pp. 1707-1711 and from Goodman and Goldman's The Pharmacological Basis of Therapeutics, Tenth Edition (2001), Appendix II, pp. 475-493.

As used herein, the term "pharmaceutically acceptable carrier" means a non-toxic, inert solid, semi-solid or liquid filler, diluent, encapsulating material or formulation auxiliary of any type that is acceptable to the patient from a pharmacological/toxicological point of view and to the manufacturing pharmaceutical chemist from a physical/ chemical point of view regarding composition, formulation, stability, patient acceptance and bioavailability. Remington's Pharmaceutical Sciences. Ed. by Gennaro, Mack Publishing, Easton, Pa., 1995 discloses various carriers used in formulating pharmaceutical compositions and known techniques for the preparation thereof. Some examples of materials which can serve as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN™ 80; buffering agents such as magnesium hydroxide and aluminium hydroxide; alginic acid; pyrogen-free water; isotonic saline; Ringer's solution; ethyl alcohol; and phosphate buffer solutions, as well as other non-toxic compatible lubricants such as sodium lauryl sulphate and magnesium stearate, as well as colouring agents, releasing agents, coating agents, sweetening, flavouring and perfuming agents, preservatives and antioxidants can also be present in the composition, according to the judgment of the formulator. If filtration or other terminal sterilization methods are not feasible, the formulations can be manufactured under aseptic conditions.

The pharmaceutical compositions of this invention can be administered to a patient by any means known in the art including oral and parenteral routes. According to such embodiments, the compositions of the invention may be administered by injection (e.g., intravenous, subcutaneous or intramuscular, intraperitoneal injection). In a particular embodiment, the recombinant adenoviruses of the present invention are administered to a subject in need thereof systemically, e.g. by IV infusion or injection. Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the recombinant adenovirus is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

The compositions can comprise the recombinant adenovirus as the only agent or in combination with another therapeutic agent.

In a preferred embodiment the composition comprises an oncolytic adenovirus or an adenovirus comprising one or more genes used in cancer gene therapy inserted in the genome of the adenovirus. In this particular case, the compositions can comprise this adenovirus as the only agent against the tumour, or in combination with another therapeutic agent such as a chemotherapy drug or a vector with an inserted therapeutic gene.

Therapeutic Uses of the Adenovirus of the Invention

There is broad experience in the use of replication-defective and replication-competent adenoviruses in the field of gene therapy and in the field of vaccination.

In a further aspect, the invention relates to a recombinant adenovirus of the invention or a pharmaceutical composition according to the invention for use in medicine. The adenoviruses of the invention may be designed to treat any kind of disease that requires the administration of such adenovirus into the bloodstream.

The inventors have also shown that the adenoviruses of the invention are particularly useful for the treatment of cancer.

In another aspect, the invention relates to a recombinant adenovirus of the invention or a pharmaceutical composition according to the invention for use in the prevention and/or treatment of cancer in a mammal, wherein the adenovirus is an oncolytic adenovirus or an adenovirus comprising one or more genes used in cancer gene therapy inserted in the genome of the adenovirus.

Alternatively, the invention relates to the use of a recombinant adenovirus of the invention or a pharmaceutical composition according to the invention for the manufacture of a medicament for the prevention and/or treatment of cancer in a mammal, wherein the adenovirus is an oncolytic adenovirus or an adenovirus comprising one or more genes used in cancer gene therapy inserted in the genome of the adenovirus.

Alternatively, the invention relates to a method for the prevention and/or treatment of cancer in a mammal comprising administering to said mammal a recombinant adenovirus of the invention or a pharmaceutical composition according to the invention, wherein the adenovirus is an oncolytic adenovirus or an adenovirus comprising one or more genes used in cancer gene therapy inserted in the genome of the adenovirus.

The term "prevention", as used herein, refers to a prophylactic or preventive method, wherein the adenovirus is administered in an initial or early stage of the disease (i.e. premalignant stage of a tumour), or to also prevent its onset.

Adenovirus vectors have been commonly used to prepare vaccines that elicit immunity against proteins of pathogens. For example, recombinant adenovirus vaccines have been publicly described against HIV, rabies virus, dengue virus, ebola virus, sars coronavirus, human papillomavirus, hepatitis C virus, hepatitis B virus, rotavirus, measles virus, respiratory syncytial virus, cytomegalovirus, herpes simplex 2 virus, Epstein barr virus, influenza virus, *Trypanosoma cruzi* and *Plasmodium falciparum*, against others.

In another aspect, the invention relates to a recombinant adenovirus of the invention or a pharmaceutical composition according to the invention for use in the prevention of an infectious disease in a mammal.

Alternatively, the invention relates to the use of a recombinant adenovirus of the invention or a pharmaceutical composition according to the invention for the manufacture of a medicament, preferably a vaccine, for the prevention of an infectious disease in a mammal.

Alternatively, the invention relates to a method for the prevention of an infectious disease in a mammal comprising administering to said mammal a recombinant adenovirus of the invention or a pharmaceutical composition according to the invention.

The expressions "infectious disease" or "infection", as used herein, refer to a disease caused by the invasion of a host organism by an infectious or pathogenic agent such as viruses, viroids and prions; microorganisms such as bacteria; parasites such as nematodes (including roundworms and pinworms), arthropods such as ticks, mites, fleas and lice; fungi and protozoa.

The recombinant adenoviruses of the invention are suitable for the manufacture of vaccines for the prevention of any kind of infectious disease.

In a preferred embodiment the infectious disease is caused by a pathogenic agent selected from the group consisting of HIV, rabies virus, dengue virus, ebola virus, sars coronavirus, human papillomavirus, hepatitis C virus, hepatitis B virus, rotavirus, measles virus, respiratory syncytial virus, cytomegalovirus, herpes simplex 2 virus, Epstein barr virus, influenza virus, *Trypanosoma cruzi* and *Plasmodium falciparum*.

The term "treat" or "treatment" refers to a therapeutic treatment, wherein the goal is to control the progression of the disease before or after the clinical signs have appeared. Control of the progression of the disease is understood as the beneficial or desired clinical results which include but are not limited to reduction of the symptoms, reduction of the duration of the disease, stabilization of pathological conditions (specifically avoiding additional impairment), delaying the progression of the disease, improving the pathological condition and remission (both partial and complete). The control of the progression of the disease also involves a prolongation of survival in comparison to the expected survival if the treatment was not applied.

For example, in the case of treating cancer, a response could be monitored by observing one or more of the following effects: (1) inhibition, to some extent, of tumour growth, including, (i) slowing down (ii) inhibiting angiogenesis and (ii) complete growth arrest; (2) reduction in the number of tumour cells; (3) maintaining tumour size; (4) reduction in tumour size; (5) inhibition, including (i) reduction, (ii) slowing down or (iii) complete prevention, of tumour cell infiltration into peripheral organs; (6) inhibition, including (i) reduction, (ii) slowing down or (iii) complete prevention, of metastasis; (7) enhancement of anti-tumour immune response, which may result in (i) maintaining tumour size, (ii) reducing tumour size, (iii) slowing the growth of a tumour, (iv) reducing, slowing or preventing invasion and/or (8) relief, to some extent, of the severity or number of one or more symptoms associated with the disorder.

The term "cancer" is referred to a disease characterized by uncontrolled cell division (or by an increase of survival or apoptosis resistance), by the ability of said cells to invade other neighbouring tissues (invasion) or by the spread to other areas of the body where the cells are not normally located (metastasis) through the lymphatic and blood vessels. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodglun's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumours such as seminoma, non-seminoma (teratomas, choriocarcinomas), stromal tumours, and germ cell tumours; thyroid cancer including thyroid adenocarcinoma and medullar carcinoma; and renal cancer including adenocarcinoma and Wilms tumour. In an embodiment the cancer is breast cancer. In another embodiment the cancer is melanoma. Other cancers will-be known to one of ordinary skill in the art.

The adenovirus of the present invention can be administered to a mammal. The term "mammal", as used herein, refers to any mammalian species, including but not being limited to domestic and farm animals (cows, horses, pigs, sheep, goats, dogs, cats or rodents), primates, and humans. Preferably, the mammal is a human being. In the context of the present invention, the mammal is suffering from cancer or in risk of suffering from cancer.

To treat tumours in animal models or patients adenoviruses can be delivered by local or regional administration through intratumoural or intracavital injection or systemically by injection into the bloodstream. The virus can also be administered in the vasculature of the tumour. Since the recombinant adenoviruses of the invention are protected against neutralizing antibodies present in the bloodstream, they are particularly suitable for systemic administration. Therefore, in a preferred embodiment the adenovirus of the invention is systemically administered. The expression "systemically administered", as used herein, refers to a route of administration into the circulatory system so that the entire body is affected. Preferably the administration is parenteral (generally intraarterial or endovenous injection, infusion or implantation).

The adenovirus of the invention is ideally administered before having been bound to serum albumin and it binds to albumin in the blood of the subject treated. However, to increase the blood persistence of adenoviruses in order to increase the possibilities of reaching the disseminated tumour nodes, the capsid can be coated with albumin before the adenovirus is administered.

The treatment of tumours with the adenoviruses of the invention can be used in combination with other therapeutic modalities like chemotherapy or radiotherapy, as previously described in the field of oncolytic adenovirus.

Protocols for using the adenoviruses described in the present invention for the treatment of cancer are the same procedures used in the fields of virotherapy and gene therapy with adenovirus.

The present invention is also directed to:

[1]. An adenoviral genome characterized in that it comprises a sequence encoding an albumin-binding moiety inserted in the coding region of a hypervariable region (HVR) of the hexon protein which results in the expression of fusion protein comprising a hexon protein and an albumin-binding moiety and wherein the albumin-binding moiety is located on the outer surface of the hexon protein when the hexon protein is assembled in the adenovirus capsid.

[2]. The adenoviral genome according to [1], wherein the genome is from a human adenovirus.

[3]. The adenoviral genome according to [2], wherein the human adenovirus is selected from the group consisting of human adenovirus serotypes 1 to 57.

[4]. The adenoviral genome according to [3], wherein the human adenovirus is serotype 5.

[5]. The adenoviral genome according to [1], [2], [3] or [4], wherein the albumin-binding moiety is selected from an albumin-binding domain from streptococcal protein G, an albumin-binding domain from *Peptostreptococcus magnus* protein PAB, an albumin-binding peptide having the core sequence DICLPRWGCLW (SEQ ID NO: 9) and functionally equivalent variants thereof.

[6]. The adenoviral genome according to [5], wherein the albumin-binding moiety is the albumin-binding domain 3 from streptococcal protein G.

[7]. The adenoviral genome according to [6], wherein the sequence of the albumin-binding domain 3 from streptococcal protein G is SEQ ID NO: 1.

[8]. The adenoviral genome according to [1], [2], [3], [4], [5], [6] or [7], wherein the HVR of the hexon protein is selected from the group consisting of HVR1, HVR2, HVR3, HVR4, HVR5, HVR6 and HVR7.

[9]. The adenoviral genome according to [8], wherein the HVR of the hexon protein is HVR1.

[10]. The adenoviral genome according to [9], wherein the sequence encoding the albumin-binding moiety is inserted so that the resulting fusion protein contains the albumin-binding moiety after the D150 amino acid of the hexon protein according to the numbering of the hexon protein having the GenBank accession number BAG48782.1 (SEQ ID NO: 27).

[11]. The adenoviral genome according to [8], wherein the HVR of the hexon protein is HVR5.

[12]. The adenoviral genome according to [11], wherein the sequence encoding the albumin-binding moiety is inserted so that the resulting fusion protein contains the albumin-binding moiety after the A274 amino acid of the hexon protein according to the numbering of the hexon protein having the GenBank accession number BAG48782.1 (SEQ ID NO: 27).

[13]. The adenoviral genome according to any of [1] to [12], wherein the N- and/or the C-terminus of the albumin-binding moiety is connected to the hexon protein by a linker sequence.

[14]. The adenoviral genome according to [13], wherein said linker sequence comprises the sequence GSGS (SEQ ID NO: 2).

[15]. The adenoviral genome according to any of [1] to [14], wherein said adenoviral genome further comprises a tissue-specific promoter or a tumour-specific promoter.

[16]. The adenoviral genome according to [15], wherein the tissue-specific promoter or the tumour-specific promoter are promoter sequences to control the expression of one or more genes selected from the group consisting of E1a, E1b, E2, and E4.

[17]. The adenoviral genome according to [16], wherein the promoter is selected from the group consisting of a E2F promoter, a telomerase hTERT promoter, a tyrosinase promoter, a prostate-specific antigen promoter, an alpha-fetoprotein promoter, and a COX-2 promoter.

[18]. The adenoviral genome according to any of [1] to [17], wherein the adenovirus is an oncolytic adenovirus.

[19]. The adenoviral genome according to [18], wherein said adenoviral genome further comprises mutations in one or more genes selected from the group consisting of E1a, E1b, E4, and VA-RNAs, to achieve selective replication in tumours.

[20]. The adenoviral genome according to any of [1] to [19], wherein the adenoviral genome further comprises capsid modifications to increase adenovirus infectivity or to target it to a receptor present in a tumour cell.

[21]. The adenoviral genome according to [20], wherein the modification of the capsid is the insertion of an RGD motif into the H1 loop of the adenoviral fiber protein.

[22]. The adenoviral genome according to any of [1] to [21], wherein the adenoviral genome comprises one or more further genes inserted in said genome.

[23]. The adenoviral genome according to [22], wherein the further genes are one or more non-adenoviral genes used in gene therapy or in vaccination.

[24]. The adenoviral genome according to [23], wherein said genes are genes used in cancer gene therapy.

[25]. The adenoviral genome according to [24], wherein said genes used in cancer gene therapy are at least a gene selected from the group consisting of prodrug-activating genes, tumour-suppressor genes, genes encoding anti-tumour interfering RNAs and immunostimulatory genes.

[26]. A recombinant adenovirus having an adenoviral genome according to any of [1] to [25].

[27]. A pharmaceutical composition comprising a therapeutically effective amount of a recombinant adenovirus according to [26] together with a pharmaceutically acceptable carrier.

[28]. A recombinant adenovirus according to [26] or a pharmaceutical composition according to [27] for use in medicine.

[29]. A recombinant adenovirus according to [26] or a pharmaceutical composition according to [27] for use in the prevention and/or treatment of cancer in a mammal, wherein the adenovirus is an oncolytic adenovirus or an adenovirus having an adenoviral genome according to [24] or [25].

[30]. The recombinant adenovirus for use according to [28] or [29], wherein the mammal is a human being.

[31]. The recombinant adenovirus for use according to [28], [29] or [30], wherein the adenovirus is systemically administered.

The following examples are provided as merely illustratives and are not to be construed as limiting the scope of the invention.

EXAMPLES

Materials and Methods

Cell lines. HEK293 (human embryonic kidney), A549 (human lung adenocarcinoma), Sk-mel28 (melanoma), and MCF7 (human breast adenocarcinoma) cells were obtained from the American Type Culture Collection (ATCC, Manassas, Va.). All tumour cell lines, excluding MCF7, were maintained with Dulbecco's Modified Eagle's Medium supplemented with 5% fetal bovine serum at 37° C., 5% $CO_2$. MCF7 cells were maintained with RPMI 1640 medium supplemented with 10% fetal bovine serum. All cell lines were routinely tested for mycoplasma presence.

Viruses construction. ICOVIR15 oncolytic adenovirus has been previously described (Rojas J J, et al. Minimal RB-responsive E1A promoter modification to attain potency, selectivity, and transgene-arming capacity in oncolytic adenoviruses. Mol Ther 2010; 18 (11):1960-71). AdGL is a E1-deleted first generation vector expressing the EGFP-Luciferase fusion protein cassette from pEGFPLuc (Clontech). Insertion of the CMV promoter –EGFPLuc-polyA cassette replacing the E1 region was performed following a recombineering protocol adapted from Stanton et al. (Stanton R J, et al. Re-engineering adenovirus vector systems to enable high-throughput analyses of gene function. Biotechniques 2008; 45(6):659-62, 664-8) based on homologous recombination in bacteria using a positive-negative selection. The CMV-GFPLuc cassette flanked with E1 homologous regions was used to replace the positive-negative selection markers of pAd5-CV5-E3+, commonly used to construct E1-deleted adenovirus vectors. ICOVIR15 was propagated in A549 cells and the replication-deficient AdGL was propagated in HEK293 cells.

ICOVIR15-ABD and AdGL-ABD were constructed by inserting the Albumin-binding domain (ABD) flanked by two linkers (GSGS) (SEQ ID NO: 2) in the hyper-variable region 1 (HVR1) of the adenovirus hexon after the D150 amino acid. The nucleotide sequence of the complete modified hexon having ABD inserted in HVR1 (ABD-HVR1) is SEQ ID NO: 3. All modifications were performed following a recombineering protocol adapted from Stanton et al. (Stanton R J, et al. Re-engineering adenovirus vector systems to enable high-throughput analyses of gene function. Biotechniques 2008; 45(6):659-62, 664-8) based on homologous recombination in bacteria using a positive-negative selection with the RpsL-Neo cassette.

First, the rpsLNeo cassette was amplified by PCR from pJetRpsLNeo, a plasmid containing the rpsLneo positive-negative selection markers cloned into pJet1.2/blunt (Genscript, Wheelock House, Hong Kong), using oligonucleotides HVR1rpsLF 5'-GCCCTGGCTCCCAAGGGTGCCC-CAAATCCTTGCGAATGGGGCCTGGTGATGATGGC-3' (SEQ ID NO: 12) and HVR1rpsLR 5'-GTAATATT-TATACCAGAATAAGGCGCCTGCCCAAATACGT-GAGTTCAGAAGAACTCGTCAAGAAG-3' (SEQ ID NO: 13). The cassette was inserted in the HVR1 of pAdZICO-VIR15 and pAdZGL plasmids creating pAdZICOVIR15-H1-rpsLNeo and pAdZGL-H1-rpsLNeo. Second, the Linker-ABD-Linker fragment was generated by PCR using the following overlapping oligonucleotides:

| Oligo-nucleotide | Sequence | SEQ ID NO: |
|---|---|---|
| ABDH1F | 5'-CCCAAGGGTGCCCCAAATCCTTGCGAATGGGATGAAGCTGCTAC TGCTCTTGAAATAAACCTAGAAGAAGAGGACGGCAGCGGATCCCTG-3' | 14 |
| ABDR1 | 5'-CCCGGTTCGCAAGCACCTTAGCCTCGGCCAGGGATCCGCTGCCC CATTC-3 | 15 |
| ABDF2 | 5'-GCTTGCGAACCGGGAACTAGACAAATACGGTGTTTCTGATTATT ACAAG-3 | 16 |
| ABDR2 | 5'-CGACGGTTTTGGCATTGTTAATCAAATTCTTGTAATAATCAGAA ACACCG-3' | 17 |
| ABDF3 | 5'-ATGCCAAAACCGTCGAGGGCGTAAAGGCTCTGATCGACGAAATA CTTGCG-3' | 18 |
| ABDR3 | 5'-ATACGTGAGTGCTACCAGACCCGGGTAGGGCCGCAAGTATTTCG TCGATC-3' | 19 |
| ABDH1R | 5'-CAGAATAAGGCGCCTGCCCAAATACGTGAGTTTTTTGCTGCTCA GCTTGCTCGTCTACTTCGTCTTCGTTGTCATCGCTACCAGACCCGGG-3' | 20 |

This fragment was used to replace the rpsLNeo cassette in both plasmids creating pAdZICOVIR15-H1-ABD and pAdZGL-H1-ABD.

Also, the ABD was inserted in the hyper-variable region 5 of AdGL after the A274 aminoacid. The nucleotide sequence of the complete modified hexon having ABD inserted in HVR5 (ABD-HVR5) is SEQ ID NO: 4. For this purpose, the rpsLNeo cassette was amplified by PCR from pJetRpsLNeo using oligonucleotides H5rpsLF and H5rpsLR as follows

| Oligo-nucleotide | Sequence | SEQ ID NO: |
|---|---|---|
| H5rpsLF | 5'-gaaagctagaaagtcaagtggaaatgcaa tttttctcaactggcctggtgatgatggc-3' | 21 |
| H5rpsLR | 5'-gtttctatatctacatcttcactgtacaa taccactttaggtcagaagaactcgtcaagaa g-3' | 22 | and inserted in pAdZGL plasmid, creating the pAdZGL-H5-rpsLNeo. In a second recombination step, the Linker-ABD-Linker fragment was amplified by PCR from pAdZICO-VIR15-H1-ABD using oligonucleotides ABDH5F and ABDH5R as follows:

| Oligo-nucleotide | Sequence | SEQ ID NO: |
|---|---|---|
| ABDH5F | 5'-ctggccgaggctaaggtgcttgcgaaccgggaactagacaaatacgg tgtttctgattattacaagaatttgattaacaatgccaaaaccgtcg agggcgtaaaggctctgatcgacgaaatacttgcggccctaccc-3' | 23 |

-continued

| Oligo-nucleotide | Sequence | SEQ ID NO: |
|---|---|---|
| ABDH5R | 5'-ctggccgaggctaaggtgcttgcgaaccgggaactagacaaatacggtgtttctgattattacaagaatttgattaacaatgccaaaaccgtcgagggcgtaaaggctctgatcgacgaaatacttgcggccctaccc-3' | 24 |

This fragment was used to replace the rpsLNeo of pAdZGL-H5-rpsLNeo creating the pAdZGL-H5-ABD.

Additionally, the domain could also be inserted in any of the hypervariable regions of the hexon protein. To do so, the rpsLNeo should be inserted in the desired region and then replaced by the ABD fragment generated by PCR with homology arms to recombine in the specific hypervariable loop.

ICOVIR15-ABD (ABD in HVR1), AdGL-ABD (ABD in HVR1), and AdGL-H5-ABD (ABD in HVR5) were generated by transfection of the generated plasmids with calcium phosphate standard protocol in HEK293 cells. Oncolytic adenovirus ICOVIR15-ABD was plaque-purified and further amplified in A549 cells. Adenoviral vector AdGL-ABD was plaque-purified and further amplified in HEK293 cells. Both viruses were purified using a cesium chloride double-gradient according to standard techniques.

Incubation of viruses with human serum albumin (HSA) was performed for one hour at room temperature with medium containing 1 mg/ml of HSA.

Viral production assay. A549 cells were infected with 800 viral particles (vp) per cell of each virus to obtain a 80-100% of infection. Cells were washed thrice with PBS 4 hours after the infection and incubated with fresh medium. At the indicated time points, cells were collected and frozen-thawed three times to obtain the cell extract. Viral titers were obtained by an antihexon staining-based method (Cascallo M, et al. Systemic toxicity-efficacy profile of ICOVIR-5, a potent and selective oncolytic adenovirus based on the pRB pathway. Mol Ther 2007; 15:1607-15) in HEK293 cells.

In vitro cytotoxicity assays. Cytotoxicity assays were performed by seeding 10,000 HEK293, 30,000 A549, 10,000 Sk-mel28 and 20,000 MCF-7 cells per well in 96-well plates. Prior to the infection, viruses were incubated for one hour at room temperature with either medium or medium containing 1 mg/ml of human serum albumin (HSA). Cells were infected in normal medium or in albumin-containing medium with serial dilutions (⅓ for HEK293, Sk-mel28 and MCF-7 cells, and ⅕ for A549 cells) starting with 10,000 vp/cell. At day 7 post-infection plates were washed with PBS and stained for total protein content (bicinchoninic acid assay; Pierce Biotechnology, Rockford, Ill.) and absorbance was quantified. The vp per cell required to produce 50% growth inhibition ($IC_{50}$) was determined from dose-response curves by standard nonlinear regression (GraFit; Erithacus Software, Horley, UK), using an adapted Hill equation.

Detection of binding to Human and Mouse Serum Albumin. Detection of binding to human serum albumin (HSA) and mouse serum albumin (MSA) was performed following an ELISA protocol adapted from Konig and Skerra (Konig T, Skerra A. Use of an albumin-binding domain for the selective immobilisation of recombinant capture antibody fragments on ELISA plates. J Immunol Methods 1998; 218:73-83). Incubations were performed 1 h at room temperature followed by three washing steps with 200 µl of PBS containing 0.1% Tween20, which was also the buffer used to dilute viruses and antibodies.

Figure 5A:
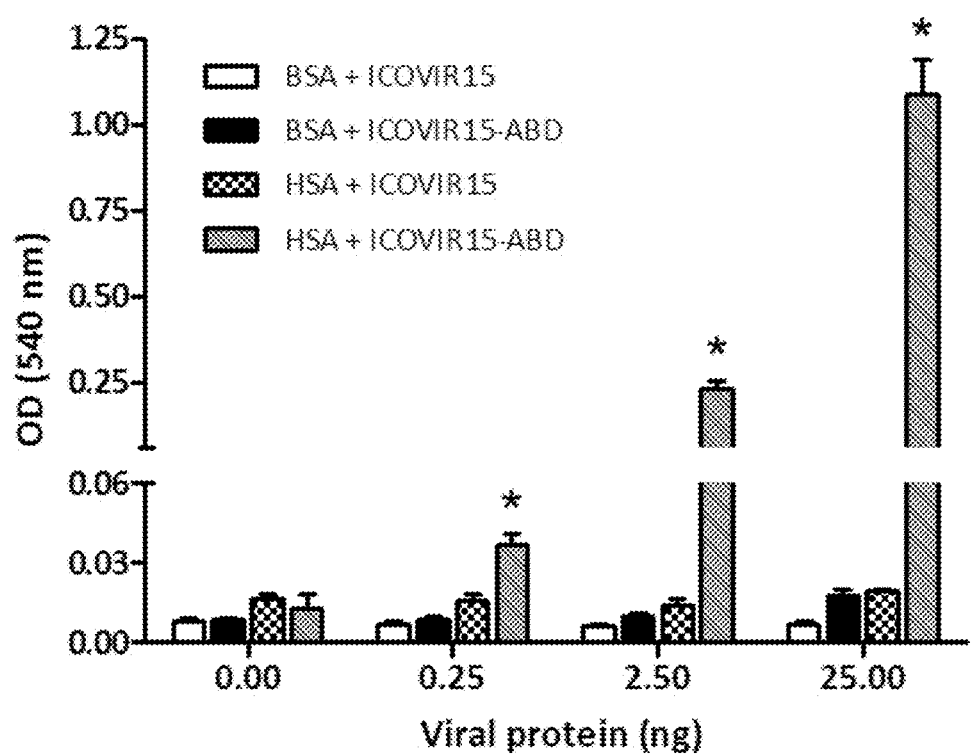
FIGS. 5A and 5B. ICOVIR15-ABD binds human and mouse albumin as detected by ELISA.

The 96-well plate was coated with 200 µl of either HSA or BSA (Sigma) at 2 mg/mL diluted in PBS. Remaining binding sites on the plastic surface were blocked with 2 mg/mL of BSA diluted in PBS containing 0.5% Tween20. In the next step, the purified viruses were added in a volume of 50 µl. Three different amounts of viral protein were tested to detect the binding (25, 2.5, and 0.25 ng of viral protein) (FIG. 5A). Viral protein concentration of the purified virus samples was quantified using Bio Rad Protein assay. Detection of viruses was performed with antihexon antibody from 2Hx-2 hybridoma (ATCC® HB-8117™) supernatant (50 µl per well at a dilution of ⅕) and a polyclonal goat anti-mouse conjugated with horseradish peroxidase (50 µl per well at a dilution of 1/2000). Wells were stained adding 100 µl per well of freshly mixed 3,3',5,5'-tetramethylbenzidine peroxidase substrate solution and incubated 15 min with shaking. The reaction was stopped adding 100 µl of sulphuric acid 2N and the absorbance was measured at 450 nm.

Figure 5B:
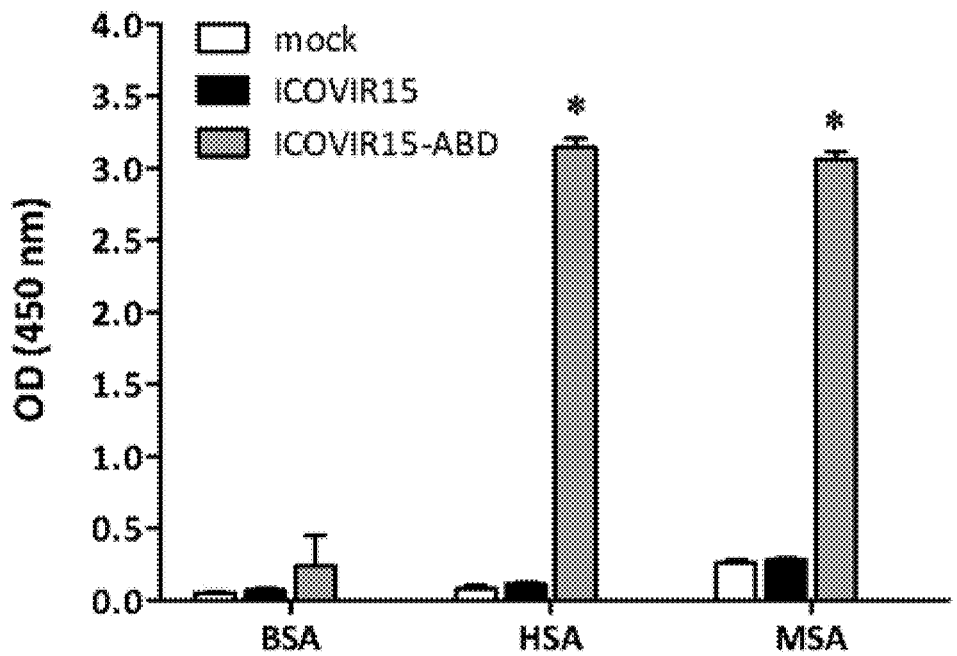

The same experiment was carried out coating a 96-well plate with 200 µl of either BSA, HSA or MSA (Sigma) at 2 mg/mL diluted in PBS and testing 25 ng of viral protein to detect the binding. A control mock group without virus was included (FIG. 5B).

In vitro antibody-mediated neutralization assays. Antibody-mediated neutralization was analysed at the level of infection (transduction with luciferase-GFP reporter adenoviruses) and replication (cytotoxicity mediated by replication-competent adenoviruses). The commercial antibody Ab6982 (Anti-Ad5 rabbit polyclonal, Abcam) was used as a neutralizing antibody. For the infectivity analysis, starting from a 1/100 dilution of the antibody stock, serial dilutions ⅙ of the antibody were performed in medium containing the different adenoviruses (AdGL or AdGL-ABD) in 96-well plates.

After one hour of incubation at room temperature, 1E5 HEK293 or 3E4 Sk-mel28 cells per well were added to obtain the desired multiplicity of infection (0.5 TU/cell or 10 vp/cell for HEK293 cells and 40 vp/cell for Sk-mel28 cells). Twenty-four hours after the infection, medium was removed and cells were lysed adding 50 µl of Cell Lysis reagent (Promega, Madison, Wis.) and frozen-thawed once. Lysates were centrifuged at 13,000 g for 5 minutes at 4° C. and the luciferase enzyme activity of the supernatant was measured using Luciferase Assay Reagent (Promega) in a luminometer (Berthold Junior, Berthold GmbH&Co, KG, Germany).

For the analysis of replication, a serial dilution ½ of the antibody was performed starting from a 1/100 dilution of the antibody stock. This serial dilution was performed using medium containing ICOVIR15 or ICOVIR15-ABD. One hour after incubation with the antibody at room temperature, 3E5 A549 cells per well were added to obtain a multiplicity of infection of 600 vp/cell. At day 4 post-infection cell viability was analyzed by staining the total protein content as described above in "in vitro cytotoxicity assays" material and methods section.

In vivo blood clearance. In vivo studies were performed at the ICO-IDIBELL facility (Barcelona, Spain) AAALAC unit 1155, and approved by IDIBELL's Ethical Committee for Animal Experimentation. Balb/C nu/nu female mice were injected intravenously with a mixture of ICOVIR15 and ICOVIR15-ABD (ratio 1:1) with a total dose of $5\times10^{10}$ vp in a volume of 10 ml/kg in PBS (n=5). At 5 min, 15 min, 1 h, 4 h, and 24 h post-administration, blood samples were collected from the tail vein. Blood samples were centrifuged at 5000 g for 5 minutes at 4° C. to separate the cell fraction and collect the serum. Serum samples were digested with proteinase K and SDS for 45 minutes at 54° C. and later for 10 minutes at 90° C. to proteolyze the capsid and release the viral DNA. Digested samples were amplified by PCR using hexon HVR1-flanking oligonucleotides Ad19121F 5'-CTGGACATGGCTTCCACGTA-3' (SEQ ID NO: 25) and Ad19300R 5'-GCTCGTCTACTTCGTCTTCG-3' (SEQ ID NO: 26), and analysed by electrophoresis on a 1% agarose gel. As ICOVIR15-ABD has the insertion of ABD in the middle of HVR1, the size of the PCR product will be longer: the PCR product expected from ICOVIR15-ABD is 361 bp compared to 199 bp from ICOVIR15.

In vivo antitumoural efficacy. Subcutaneous melanoma xenograft tumours were established by injection of $1\times10^{7}$ Sk-mel28 cells into the flanks of 6-week-old female Balb/C nu/nu mice. When tumours reached 150 mm$^3$ (experimental day 0), mice were randomized (n=10 to 12 animals per group) and were injected with a single intravenous administration of PBS or $5\times10^{10}$ vp of ICOVIR15 or ICOVIR15-ABD in a volume of 10 ml/kg in PBS via tail vein. Tumour size and mice status were monitored thrice per week. Tumour volume was measured with a digital calliper and defined by the equation $V(mm^3)=\pi/6\times W^2\times L$, where W and L are the width and the length of the tumour, respectively. The statistical significance of differences in tumour size between treatment groups was assessed by a two-tailed Student's unpaired t-test.

In vivo transduction. Melanoma tumors were established implanting $1\times10^{6}$ B16-CAR cells subcutaneously into both flanks of 6-week-old female C57BL6 mice (n=4-6 animals per group). When tumors reached 100 mm$^3$, mice were injected intraperitoneally with either PBS (naïve group) or with $2\times10^{10}$ vp of hAd5wt (preimmunized group). Seven days after-immunization, animals were injected with a single intravenous administration of PBS, AdGL, or AdGL-ABD at a dose of $3\times10^{10}$ viral particles per mouse. Three days after vector injection mice received an intraperitoneal injection of 250 μL of D-Luciferin (15 mg/mL; Biosynth, Staad, Switzerland) and mice were sacrificed for liver and tumor harvesting for bioluminescent imaging (IVIS). Organs were imaged on the IVIS Lumina XR (Caliper Life Sciences, Hopkinton, Mass.) and the Living Image v4.0 software was used to quantify the emission of light.

Results

Figure 1:
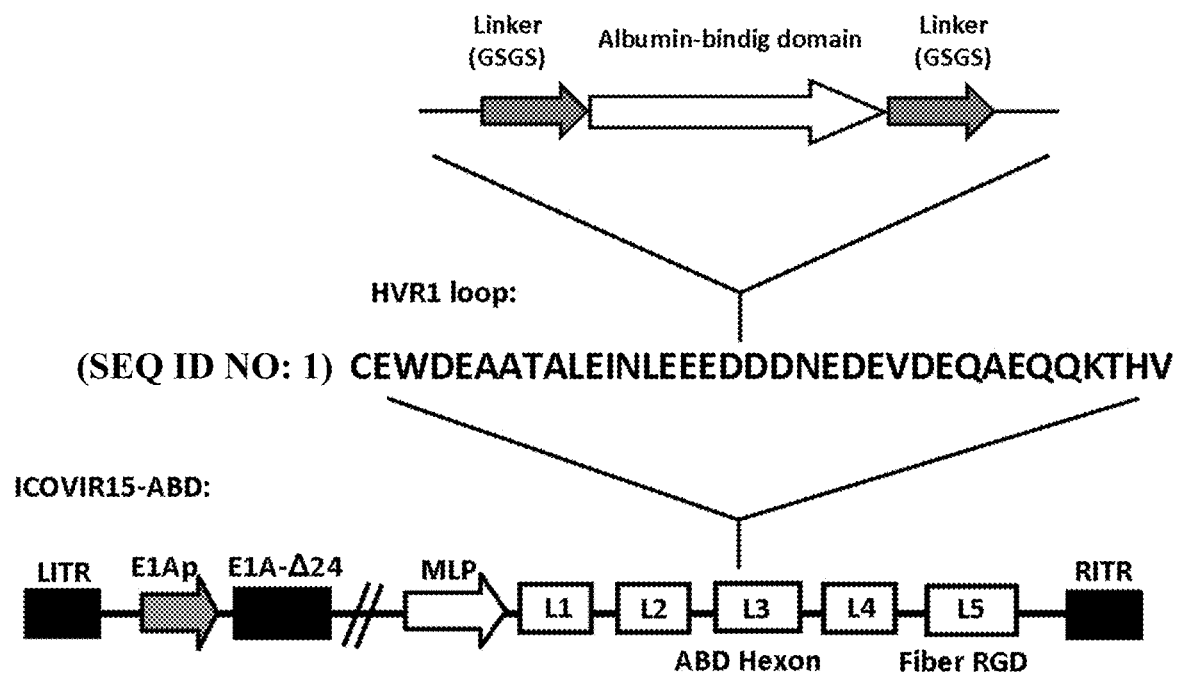
FIG. 1. Schematic diagram of albumin-binding domain (ABD) insertion in ICOVIR15-ABD. The ABD 3 from streptococcal protein G (SEQ ID NO: 1) is flanked by two GSGS (SEQ ID NO: 2) linkers and inserted in the middle of the hypervariable region 1 (HVR1) of hexon of oncolytic adenovirus ICOVIR15 obtaining ICOVIR15-ABD. LITR/RITR, left and right inverted terminal repeats; MLP, major late promoter; E1Ap, modified E1A promoter; E1A-Δ24, mutant version of E1A protein where amino acids 121-129 of the polypeptide chain have been deleted; L1 to L5, late genes; Fiber RGD, RGD-modified fiber by insertion of the RGD peptide at the H11-loop of the fiber.
Figure 2:
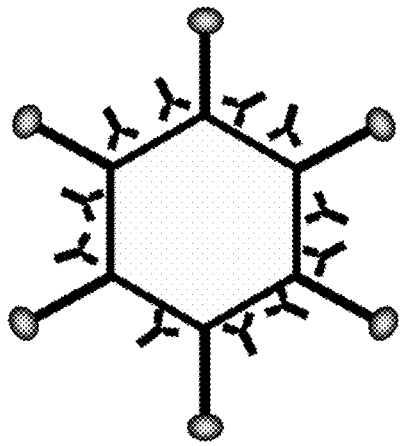
FIG. 2. Drawing of an adenovirus containing an albumin binding domain (ABD) inserted in the hexon. Compared to a non-modified adenovirus ICOVIR15 (left), the ABD-modified virus ICOVIR-15-ABD (right) is coated with albumin present in blood, shielding the virus from neutralizing antibodies.
Figure 2:
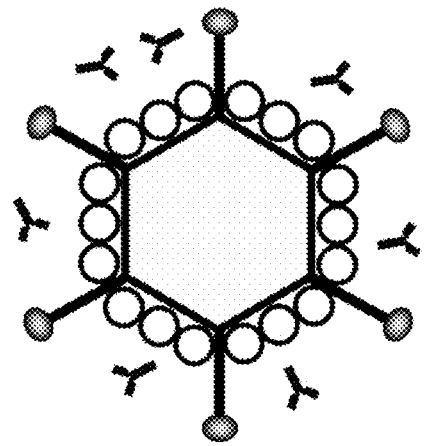

Generation and characterization of ICOVIR15-ABD. To generate an albumin-binding adenovirus, the albumin-binding domain 3 from the protein G of streptococcus bacteria (SEQ ID NO: 1) was inserted in the HVR1 of ICOVIR15 hexon, generating the oncolytic adenovirus ICOVIR15-ABD (FIGS. 1 and 2). The domain was inserted flanked by two linkers (GSGS) (SEQ ID NO: 2) in the middle of the HVR1 after the D150 amino acid without deleting any hexon sequence (FIG. 1).

Figure 3:
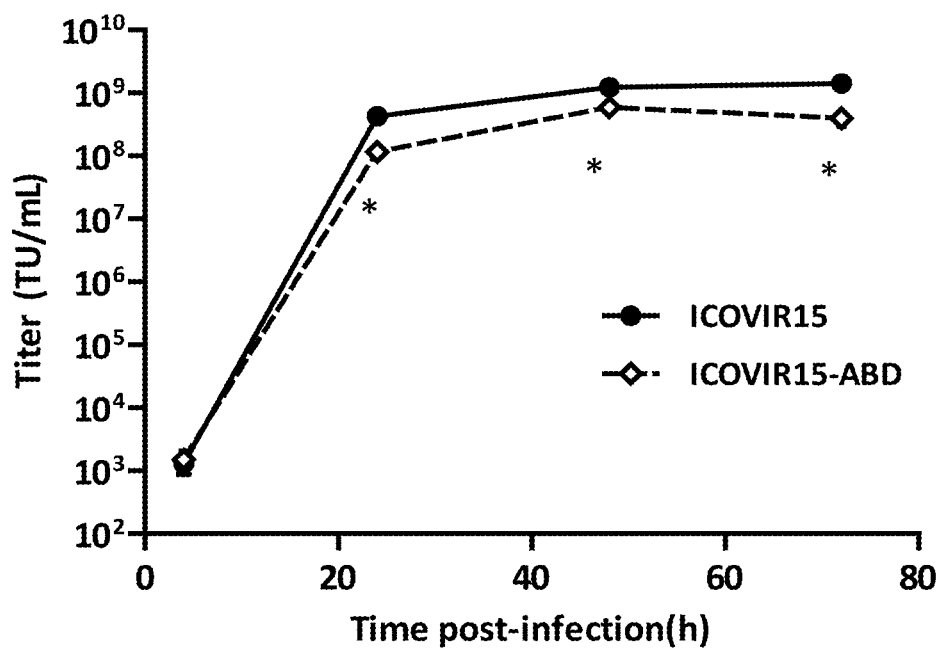
FIG. 3. Viral production kinetics of ICOVIR15-ABD and ICOVIR15. Confluent A549 cells were infected with 800 viral particles (vp) per cell. Four hours (h) after the infection the virus was removed, cells were washed thrice with PBS and incubated with virus-free medium. Cell extracts were collected 4, 24, 48, and 72 hours after the infection and titrated by antihexon staining-based method. Samples were evaluated in triplicate. Mean±SD error bars are plotted (although these are difficult to distinguish because their low values). TU/mL, transducing units per mL. * Statistical significance compared to ICOVIR15 group (p≤0.05).
Figure 4:
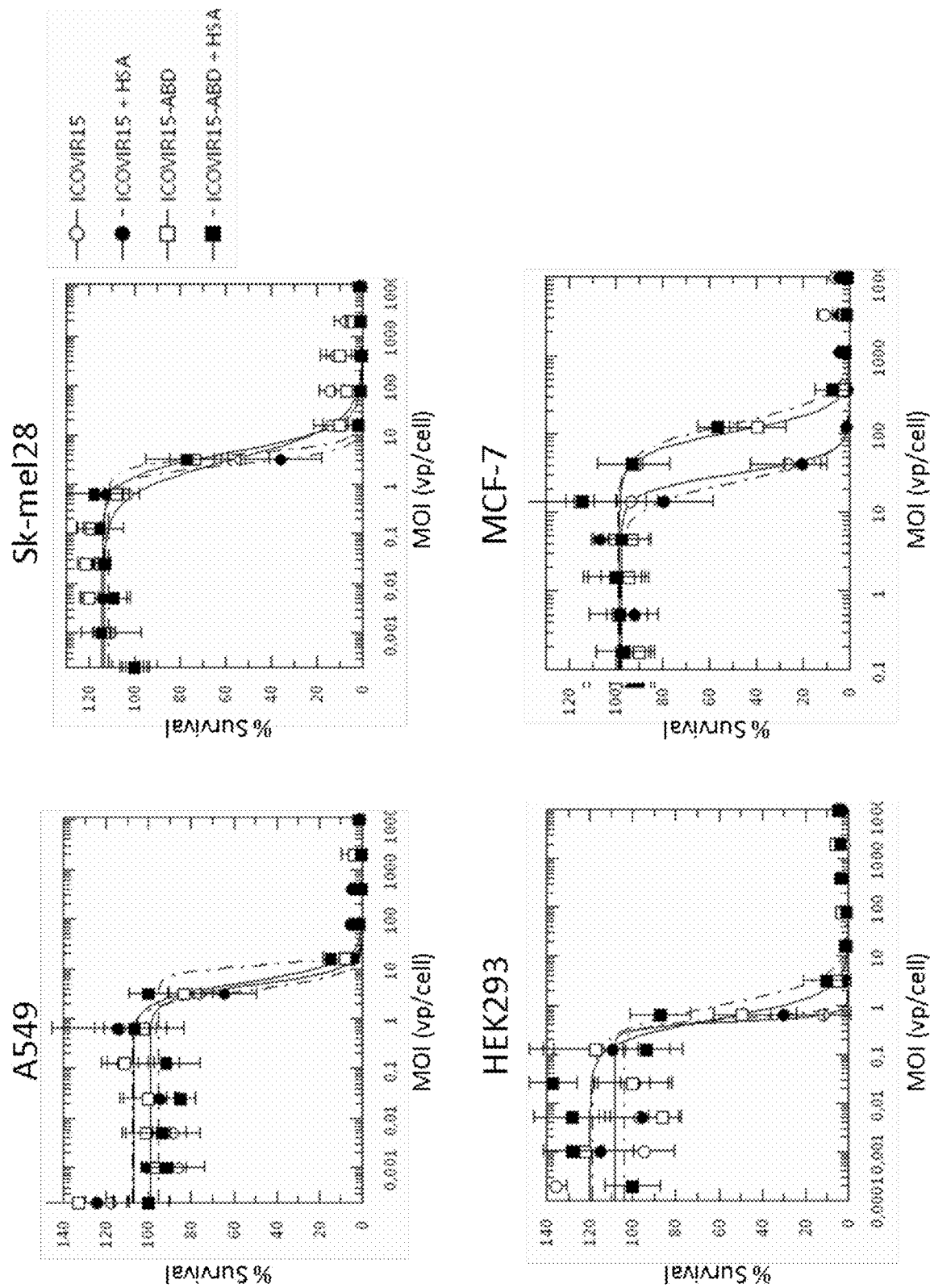
FIG. 4. Comparative cytotoxicity in vitro of ICOVIR15 and ICOVIR15-ABD in presence or absence of human serum albumin (HSA). A549, Sk-mel28, HEK293 and MCF-7 cells were infected with the indicated viruses from 10000 to 0.0001 viral particles (vp) per cell. IC50 values (vp per cell required to cause a reduction of 50% in cell culture viability) at day 7 after infection are shown. Three different replicates were quantified for each cell line. Mean±SD error bars are plotted. MOI, multiplicity of infection.

To analyze the impact of the ABD insertion on virus replication, we compared the replication kinetics of ICOVIR15 and ICOVIR15-ABD in A549 cells. As shown in FIG. 3, even though the kinetics of production of both viruses were similar, a reduction in the total production yield of ICOVIR15-ABD was observed. Virus ability to kill cancer cells in vitro was also analyzed. Cytotoxicity experiments were performed in HEK293, A549, Sk-mel28 and MCF-7 cells, in presence or absence of HSA. $IC_{50}$ values indicated no significant differences among viruses in three out of four cell lines tested, and a 3-fold $IC_{50}$ increase for ICOVIR15-ABD compared to ICOVIR15 in MCF-7 cells, indicating a certain loss of cytotoxicity in this cell line (FIG. 4). Addition of HSA did not affect the cytotoxicity in any case.

An ELISA experiment was performed to demonstrate binding of ICOVIR15-ABD to HSA and MSA. Wells were coated with either MSA, HSA or BSA (note that ABD binds to MSA and HSA, but not to BSA) and binding of both viruses ICOVIR15 or ICOVIR15-ABD was analyzed. Positive signal was obtained when adding ICOVIR15-ABD to both HSA-coated wells (FIG. 5A) and MSA-coated wells (FIG. 5B) and the intensity of the signal increased with the amount of virus used (FIG. 5A). When BSA was used instead of HSA or MSA, no signal was observed regardless of the amount of virus added, indicating that the virus can bind to human and murine but not to bovine albumin. As expected, no binding was detected with ICOVIR15 virus in any case.

Albumin-binding protects adenovirus from neutralizing antibodies in vitro. Having demonstrated the binding of ICOVIR15-ABD to human albumin, the inventors tested if this binding could protect the virus from neutralizing antibodies (NAbs) in vitro. For this, an adenovirus vector expressing a GFP-Luciferase fusion protein modified with ABD at the hexon, named AdGL-ABD, was constructed. The transduction efficiency of AdGL-ABD in HEK293 cells was studied, after incubation with serial dilutions of the commercial neutralizing antibody Ab6982 (rabbit polyclonal antibody against Ad5) in presence and absence of HSA. As shown in FIG. 6, similar levels of transduction were achieved with the non modified AdGL vector regardless of albumin incubation. In contrast, HSA protected AdGL-ABD from neutralization. Interestingly, the AdGL-ABD was less neutralized than the non-modified vector AdGL even when not incubated with albumin, indicating that the mere modification of the HVR1 with the ABD already precluded binding of some NAbs.

Figure 7:
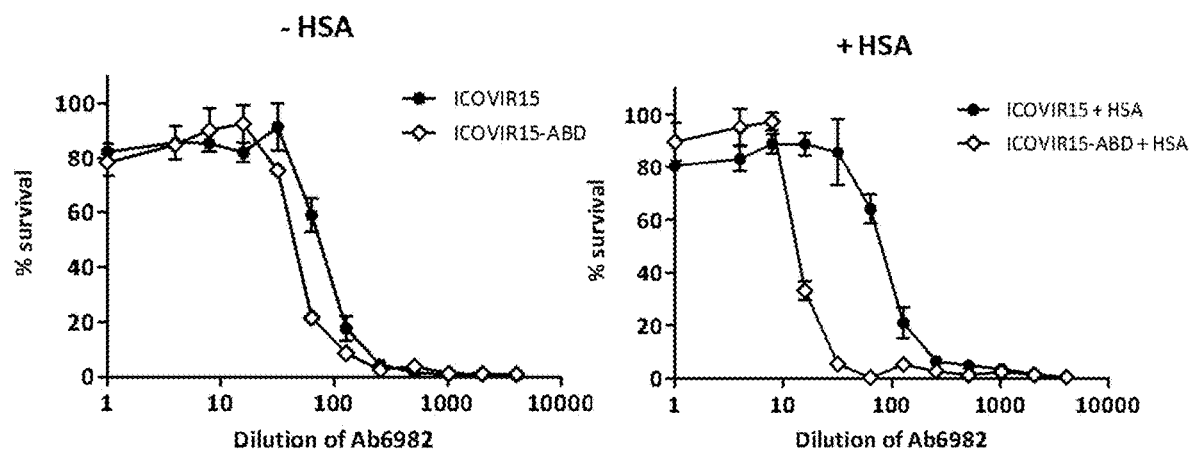
FIG. 7. ICOVIR15-ABD shows an increased in vitro cytotoxicity in presence of neutralizing antibodies when protected with human serum albumin (HSA). ICOVIR15 and ICOVIR15-ABD were incubated with serial dilutions of the neutralizing antibody Ab6982 (Nab, commercial polyclonal anti-HAd5) for 1 hour in presence or absence of Human Serum Albumin (HSA). A549 cells were added to obtain a multiplicity of infection of 600 viral particles (vp) per cell. The percentage of surviving cells (protein content in the wells) was measured at day 4 post-infection. Samples were evaluated in triplicate. Mean±SD error bars are plotted.

In addition, the capacity of viruses to kill cancer cells in presence of neutralizing antibodies was also analyzed. For this purpose, A549 cells were infected with ICOVIR15 or ICOVIR15-ABD previously incubated with serial dilutions of the neutralizing antibody Ab6982 in presence and absence of HSA, and cell survival was analyzed 4 days after the infection. In absence of human albumin both viruses showed similar capacity to kill tumor cells (FIG. 7), and only a small increase of cytotoxicity was observed with ICOVIR15-ABD probably due to the certain evasion of neutralizing antibodies observed in transduction (FIG. 6). Importantly, when human albumin was added to the media the cytotoxicity of ICOVIR15-ABD was significantly enhanced in contrast to that of ICOVIR15 which remained unaltered.

Figure 8:
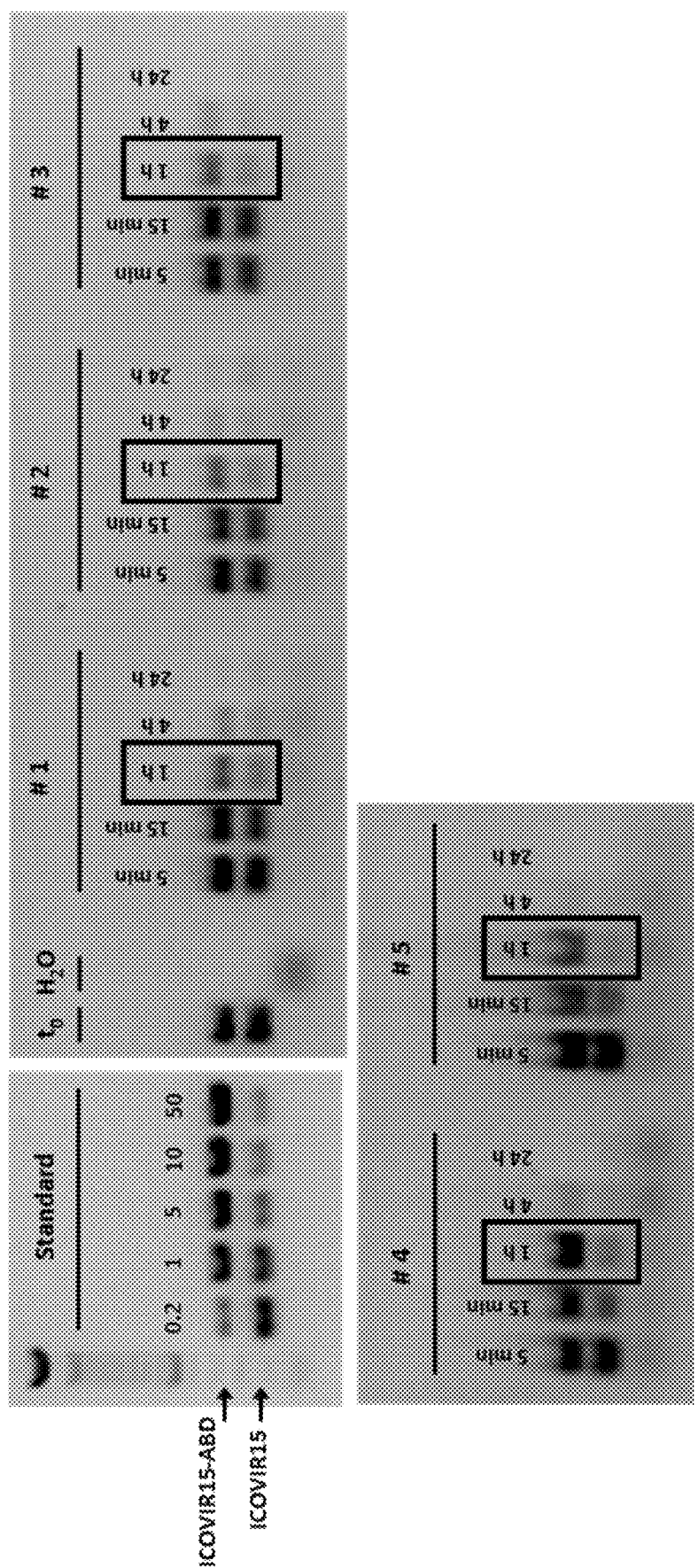
FIG. 8. ABD insertion increases the adenovirus plasma half-life. Nude mice were injected with a mixture of ICOVIR15 and ICOVIR15-ABD at a ratio 1:1 with a total dose of $5 \times 10^{10}$ viral particles (vp) per mouse (n=5). Blood samples were collected 5, 15 min, 1, 4, and 24 hours after administration and centrifuged to collect the serum. PCR amplification of the hypervariable region 1 (HVR1) of adenovirus hexon was performed and samples were analyzed by electrophoresis. The ABD insertion increases the size of the HVR1 from 299 to 361 bp. The gel shows a standard with several ratios of ICOVIR15-ABD: ICOVIR15 genomes (0.2, 1, 5, 10 and 50), a pre-injection control (to), a water negative-control of the PCR ($H_2O$), and the PCR of the serum samples (#1 to #5).

ICOVIR15-ABD displays an increased plasma half life. To investigate whether albumin-binding can reduce the rapid blood clearance of adenovirus, the pharmacokinetics of ICOVIR15-ABD after systemic administration in vivo was studied. Mice were injected with a mixture of ICOVIR15 and ICOVIR15-ABD at a ratio 1:1 with a total dose of $5\times10^{10}$ viral particles per mouse, and blood samples were collected at different time points. Amplification of hexon HVR1 was performed by PCR in serum samples. Because of the ABD insertion, a 361 bp band is obtained with ICOVIR15-ABD whereas with ICOVIR15 the size of the band is only 199 bp. Hence, comparing the relative intensity of the bands at each time point it was possible to determine which virus persists longer in the bloodstream. FIG. 8 shows the electrophoresis of the PCR reactions of all samples including a standard with several ratios of ICOVIR15-ABD: ICOVIR15 (0.2, 1, 5, 10 and 50), the pre-injection control, and the water negative control. Equally intense bands were obtained in the pre-injection control and 5 minutes after the injection. From then on, a shift on the intensity of the bands can be seen as the band corresponding to ICOVIR15-ABD becomes more intense than the ICOVIR15 one. At 1 h after the injection the differential persistence of both viruses is clearly evident in favour of ICOVIR15-ABD. These data indicate that after 5 minutes post-injection ICOVIR15 is cleared from the bloodstream much quicker than ICOVIR15-ABD, demonstrating the improved pharmacokinetics of the ABD-modified virus.

Figure 9:
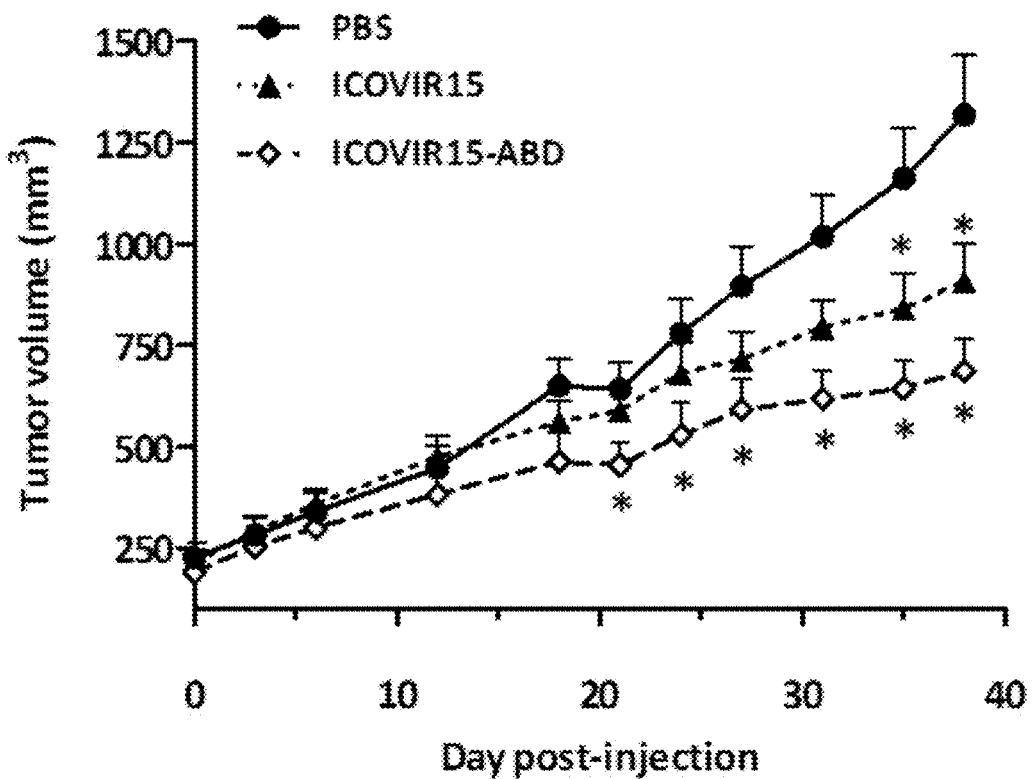
FIG. 9. Anti-tumour activity of ICOVIR15-ABD after systemic administration in vivo. Nude mice bearing subcutaneous xenografts of melanoma (Sk-mel28) were injected with a single intravenous dose of phosphate-buffered saline (PBS), ICOVIR15 or ICOVIR15-ABD ($5 \times 10^{10}$ viral particles (vp) per mouse). Tumour volumes±SEM are plotted (n=10-12). * Statistical significance compared to PBS group (p≤0.05).

Anti-tumour activity of ICOVIR15-ABD after systemic administration in vivo. Once demonstrated the increased plasma half-life of ICOVIR15-ABD, it was tested whether this translated in an increased anti-tumour efficacy after systemic administration. Mice bearing Sk-mel28 (melanoma) xenograft tumours were injected with a single intravenous dose of phosphate-buffered saline (PBS), ICOVIR15 or ICOVIR15-ABD at $5\times10^{10}$ viral particles per mouse. At day 38 after treatment, animals were sacrificed due to the large size of PBS-treated tumours. Both viruses were able to significantly reduce the tumour growth compared with PBS (FIG. 9). However, ICOVIR15-ABD treatment showed a statistical reduction in tumour growth from day 21 until the end of treatment, whereas ICOVIR15 could not statistically control tumour growth until day 35. At day 38 when animals were sacrificed, ICOVIR15 induced a reduction of 1.4-fold compared to a 2-fold reduction with ICOVIR15-ABD.

Figure 10:
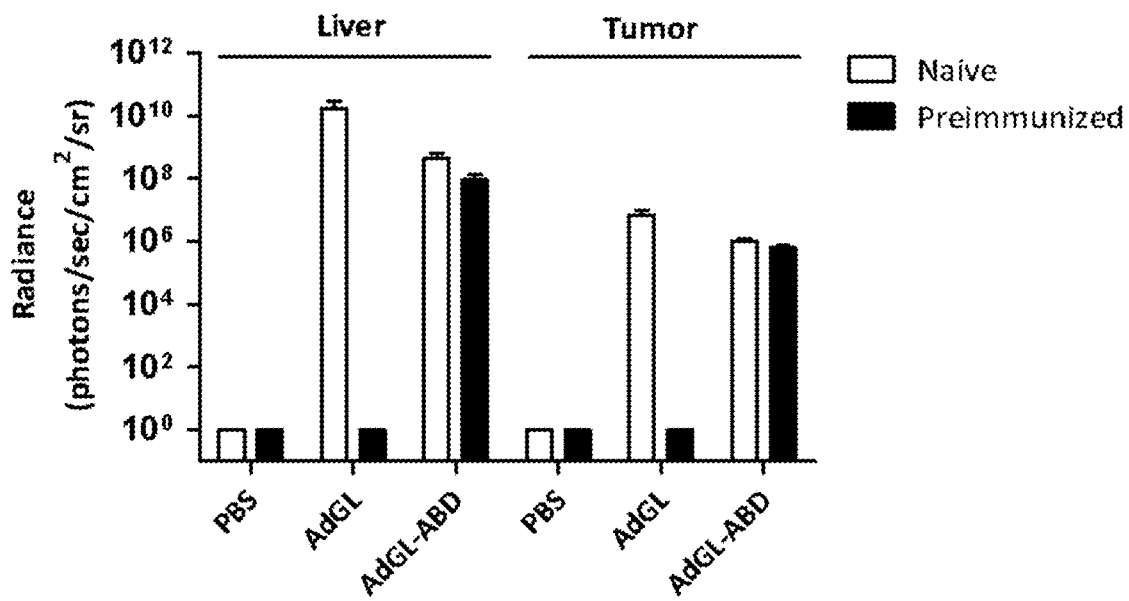
FIG. 10. In vivo liver and tumor transduction with an adenoviral vector modified with an albumin binding domain in the hexon HVR1 is preserved in adenovirus-preimmune mice. C57BL/6 mice bearing subcutaneous xenografts of melanoma (B16-CAR) were immunized with an intraperitoneal injection of hAd5wt ($2 \times 10^{10}$ viral particles (vp) per mouse) or vehicle, and 7 days later were injected intravenously with AdGL (GFP-Luciferase vector) or AdGL-ABD ($3 \times 10^{10}$ vp per mouse). Three days later luciferase activity in liver and tumor was analyzed by bioluminescence imaging (IVIS). Mean±SEM are plotted (livers n=4-6, tumors n=8-12). sec: seconds; sr: steradian.

Albumin-binding protects adenovirus from anti-HAd5 preimmunity in vivo. Immunocompetent C57BL6 mice bearing B16-CAR melanoma tumors were immunized with an intraperitoneal injection of $2\times10^{10}$ viral particles of hAd5wt or with PBS (preimmunized or naïve groups). Seven days later, mice received a single intravenous dose of PBS, AdGL, or AdGL-ABD at $3\times10^{10}$ viral particles per mouse. Three days after vector injection mice were sacrificed and liver and tumors were harvested for in vivo bioluminescent imaging (IVIS). No significant differences were observed among vectors in liver and tumor transduction in naïve animals (FIG. 10). Of note, when animals were preimmunized the non-modified AdGL vector suffered a complete neutralization as the transduction of liver and tumors was completely abolished. On the contrary, AdGL-ABD is able to maintain the same levels of transduction in liver and tumors, indicating a protection from anti-HAd5 preimmunity.

Figure 11:
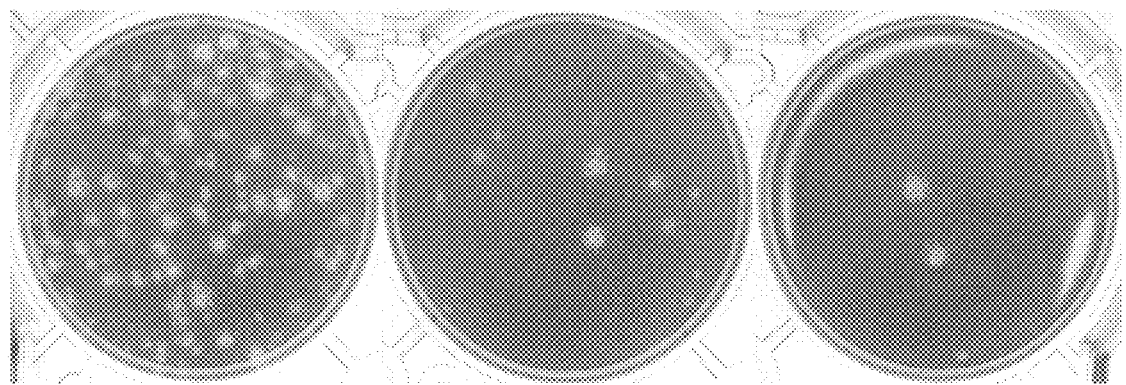
FIG. 11. ABD insertion in hypervariable-region 5 does not affect the virus viability. HEK293 cells were transfected with pAdZGL-H5-ABD plasmid to generate AdGL-H5-

Insertion of ABD in hypervariable region 5. To test whether this insertion could also be made in other hypervariable regions of the hexon we constructed the AdGL-H5-ABD vector. HEK293 cells were transfected with pAdZGL-H5-ABD plasmid to generate AdGL-H5-ABD virus. One week after transfection the cells and supernatant were harvested and lysed by three freeze-thaw cycles. The cell extract containing virus was tittered in HEK293 cells by plaque assay. Wells corresponding to dilutions 1E6, 1E7 and 1E8 are shown in FIG. 11, where plaques demonstrating virus propagation are evident. Insertion of ABD in HVR5 was confirmed by sequencing the virus genome. This demonstrates the possibility of inserting the ABD in other hypervariable regions without affecting the viability of the virus.

Insertion of ABD in hypervariable region 5 does not protect adenovirus from neutralizing antibodies. To check if the ABD inserted in the hypervariable region 5 could also protect adenovirus from neutralizing antibodies, we compared the transduction efficiency of the vectors AdGL, AdGL-H1-ABD and AdGL-H5-ABD after incubation with serial dilutions of the Ab6982 NAb with or without HSA in HEK293 and Sk-mel28 cells. As observed in FIG. 6, incubation with HSA provided a clear advantage of transduction to AdGL-H1-ABD in both cell lines, whereas it had no important effect on the non-modified vector AdGL (FIG. 12). Surprisingly, addition of human albumin did not increase the transduction levels of AdGL-H5-ABD. This indicates that the ABD is functional when inserted in HVR1 but not in HVR5.

What is claimed is:

1. A recombinant oncolytic adenovirus comprising a polynucleotide encoding a hexon protein comprising an albumin-binding moiety inserted within its hypervariable region 1 (HVR1), wherein the oncolytic adenovirus is human adenovirus serotype 5.

2. The recombinant oncolytic adenovirus according to claim 1, wherein the albumin-binding moiety is selected from an albumin-binding domain from streptococcal protein G, an albumin-binding domain from *Peptostreptococcus magnus* protein PAB, an albumin-binding peptide having the core sequence DICLPRWGCLW (SEQ ID NO: 9), and functionally equivalent variants thereof.

3. The recombinant oncolytic adenovirus according to claim 2, wherein the albumin-binding moiety is the albumin-binding domain 3 from streptococcal protein G.

4. The recombinant oncolytic adenovirus according to claim 1, wherein the hexon protein contains the albumin-binding moiety inserted after amino acid residue D150 of the hexon protein according to the numbering of the hexon protein of SEQ ID NO: 27.

5. The recombinant oncolytic adenovirus according to claim 1, wherein the N- and/or the C-terminus of the albumin-binding moiety is connected to the hexon protein by a linker sequence.

6. The recombinant oncolytic adenovirus according to claim 5, wherein said linker sequence comprises the sequence GSGS (SEQ ID NO: 2).

7. The recombinant oncolytic adenovirus according to claim 1, wherein said oncolytic adenovirus further comprises a polynucleotide encoding a tissue-specific promoter or a tumour-specific promoter.

8. The recombinant oncolytic adenovirus according to claim 1, wherein said oncolytic adenovirus further comprises mutations in one or more genes selected from E1a, E1b, E4, and VA-RNAs.

9. The recombinant oncolytic adenovirus according to claim 1, wherein the oncolytic adenovirus further comprises one or more capsid modifications to increase oncolytic adenovirus infectivity and/or to target the oncolytic adenovirus to a receptor present in a tumour cell.

10. The recombinant oncolytic adenovirus according to claim 9, wherein the one or more capsid modifications comprise insertion of an RGD motif into the H1 loop of the adenoviral fiber protein.

11. The recombinant oncolytic adenovirus according to claim 9 wherein the one or more capsid modifications comprise substitution of a region of the fiber gene with the homologous region from a different adenovirus serotype to form a chimeric adenovirus.

12. The recombinant oncolytic adenovirus according to claim 1, wherein the oncolytic adenovirus comprises one or more polynucleotides encoding one or more non-adenoviral genes and said genes are genes used in gene therapy or in vaccination.

13. The recombinant oncolytic adenovirus according to claim 12, wherein said genes are genes used in cancer gene therapy.

14. A pharmaceutical composition comprising a therapeutically effective amount of a recombinant oncolytic adenovirus according to claim 1 together with a pharmaceutically acceptable carrier.

15. A method for the treatment of cancer in a mammal comprising administering to said mammal a recombinant oncolytic adenovirus according to claim 1, wherein the oncolytic adenovirus comprises an oncolytic adenovirus comprising one or more polynucleotides encoding one or more non-adenoviral genes used in cancer gene therapy.

16. The method according to claim 15, wherein the oncolytic adenovirus is systemically administered.

* * * * *